United States Patent [19]
Kato et al.

[11] Patent Number: 5,932,550
[45] Date of Patent: Aug. 3, 1999

[54] DIPEPTIDE COMPOUND OR PHARMACEUTICALLY ACCEPTABLE SALT THEREOF AND MEDICAL USE THEREOF

[75] Inventors: Ryohei Kato; Tsutomu Mimoto; Tominaga Fukazawa; Naoko Morohashi, all of Toda; Yoshiaki Kiso, Ibaraki, all of Japan

[73] Assignee: Japan Energy Corporation, Tokyo, Japan

[21] Appl. No.: 08/669,757

[22] Filed: Jun. 26, 1996

[30] Foreign Application Priority Data

Jun. 30, 1995 [JP] Japan .................................. 7-188151
May 10, 1996 [JP] Japan .................................. 8-140678

[51] Int. Cl.[6] .......................... A61K 38/05; C07K 5/06; C07K 1/06
[52] U.S. Cl. .................... 514/19; 424/185.1; 530/333; 530/336; 530/337; 260/998.2
[58] Field of Search .................. 424/185.1; 514/19; 530/300, 331, 333, 334, 335, 336, 337, 338, 341, 342, 344, 345; 260/998.2

[56] References Cited

U.S. PATENT DOCUMENTS

| | | | |
|---|---|---|---|
| 4,963,655 | 10/1990 | Kinder et al. | 530/331 |
| 5,086,165 | 2/1992 | Marshall et al. | 530/329 |
| 5,126,326 | 6/1992 | Anderson et al. | 514/17 |
| 5,132,400 | 7/1992 | Gammill et al. | 530/317 |
| 5,145,951 | 9/1992 | Voges et al. | 530/330 |
| 5,187,074 | 2/1993 | Treiber et al. | 435/41 |
| 5,188,950 | 2/1993 | Balani et al. | 435/120 |
| 5,192,668 | 3/1993 | Treiber et al. | 435/41 |
| 5,212,157 | 5/1993 | Anderson et al. | 514/17 |
| 5,342,922 | 8/1994 | Marshall et al. | 530/329 |
| 5,434,265 | 7/1995 | Fritz et al. | 546/146 |
| 5,438,118 | 8/1995 | Callahan et al. | 530/330 |
| 5,475,013 | 12/1995 | Talley et al. | 514/311 |
| 5,476,874 | 12/1995 | Hungate et al. | 514/599 |
| 5,491,166 | 2/1996 | Kaldor et al. | 514/481 |
| 5,492,910 | 2/1996 | Barrish et al. | 514/237.5 |
| 5,502,060 | 3/1996 | Thompson et al. | 514/307 |
| 5,502,061 | 3/1996 | Hui et al. | 514/311 |
| 5,514,802 | 5/1996 | Fritz et al. | 546/146 |
| 5,644,028 | 7/1997 | Mimoto et al. | 530/331 |

FOREIGN PATENT DOCUMENTS

| | | | |
|---|---|---|---|
| 0 394 853 | 10/1990 | European Pat. Off. | C07K 5/06 |
| 0 438 311 A2 | 7/1991 | European Pat. Off. | C07K 5/02 |
| 0 490 667 A2 | 6/1992 | European Pat. Off. | C07K 5/02 |
| 0 498 680 A1 | 8/1992 | European Pat. Off. | C07D 207/16 |
| 0587311A1 | 3/1994 | European Pat. Off. | . |
| 0 604 184 A1 | 6/1994 | European Pat. Off. | C07C 323/60 |
| 0 604 185 A1 | 6/1994 | European Pat. Off. | C07D 217/26 |
| WO92/03472 | 3/1992 | WIPO | C07K 5/06 |
| WO93/02057 | 2/1993 | WIPO | 233/64 |
| WO94/18192 | 8/1994 | WIPO | C07D 401/14 |
| WO94/26749 | 11/1994 | WIPO | C07D 493/04 |
| WO95/14655 | 6/1995 | WIPO | C07C 219/02 |

OTHER PUBLICATIONS

Baldwin et al. (1995), "Structure of HIV–1 Protease With KNI–272, A Tight–Binding Transition–State Analog Containing Allophenylnorstatine," *Structure* 581–590.

Kiso (1995), "Design and Synthesis of HIV Protease Inhibitors Containing Allophenylnorstatine As A Transition–State Mimic," *Aspartic Proteinases Structure, Function, Biology and Biomedical Implications,* Ed. Kenji Takahashi, Plenum Press, NY, pp. 414–423.

Gulnik et. al. (1995), "Kinetic Characterization and Cross–Resistance Patterns of HIV–1 Protease Mutant Selected under Drug Pressure," *Biochemistry,* vol. 34, No. 29, 9282–9287.

Kageyama et al. (1993), "In Vitro Anti–Human Immunodeficiency Virus (HIV) Activities of Transition State Mimetic HIV Protease Inhibitors Containing Allophenylnorstatine," 37 *Antimicrob. Agents & Chemo.* 4:810–817.

Humphrey et al. (1997), "Removal of Human Immunodeficiency Virus Type I (HIV–1) Protease Inhibitors From Preparations of Immature HIV–1 Virions Does Not Result in an Increase in Infectivity or the Appearance of Mature Morphology," 41 *Antimicrob. Agents & Chemo.* 5:1017–1023.

(List continued on next page.)

*Primary Examiner*—Robert D. Budens
*Attorney, Agent, or Firm*—Testa, Hurwitz & Thibeault, LLP

[57] ABSTRACT

The present invention provides a novel dipeptide compound or pharmaceutically acceptable salt thereof which exhibits an excellent HIV protease inhibitory activity and an excellent bioavailability from digestive tracts, and an anti-AIDS agent comprising said dipeptide compound as an effective ingredient.

General formula (I):

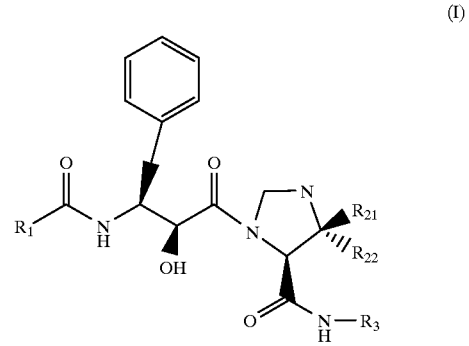

(wherein $R_1$ represents 5-membered or 6-membered monocyclic hydrocarbon group or heterocyclic group wherein more than one carbon atom of said monocyclic hydrocarbon group is substituted with hetero atom. X represents methylene group (—$CH_2$—), chloromethylene group(—CH(Cl)—), oxygen atom sulfur atom or sulfonyl group (—$SO_2$—). $R_{21}$ and $R_{22}$ each represents hydrogen atom or aliphatic hydrocarbon group having 1–6 carbons. $R_3$ represents aliphatic hydrocarbon group or monovalent group derived from aromatic monocyclic hydrocarbon having 1–6 carbons.)

16 Claims, No Drawings

OTHER PUBLICATIONS

Uchida et al. (1997), "HIV–1 Protease Does Not Play A Critical Role In The Early Stages of HIV–1 Infection," *Antiviral Research* 107–113.

Fahoy et al, *Clin. Exp. Immunol.* 88:1–5, 1992.

Fox, J.L., *Bio/Technology* 12:128, Feb. 1994.

Haynes et al., Ann. Med. 28:39–41, 1996.

Gulnik et. al. (1995), "Kinetic Characterization and Cross–Resistance Patterns of HIV–1 Protease Mutant Selected under Drug Pressure," *Biochemistry*, vol. 34, No. 29, 9282–9287.

Kageyama et al. (1993), "In Vitro Anti–Human Immunodeficiency Virus (HIV) Activities of Transition State Mimetic HIV Protease Inhibitors Containing Allophenylnorstatine," 37 *Antimicrob. Agents & Chemo.* 4:810–817.

Humphrey et al. (1997), "Removal of Human Immunodeficiency Virus Type I (HIV–1) Protease Inhibitors From Preparations of Immature HIV–1 Virions Does Not Result in an Increase in Infectivity or the Appearance of Mature Morphology," 41 *Antimicrob. Agents & Chemo.* 5:1017–1023.

Uchida et al. (1997), "HIV–1 Protease Does Not Play A Critical Role In The Early Stages of HIV–1 Infection," 36 *Antiviral Research* 107–113.

N.A. Roberts et al., "Rational Design of Peptide–Based HIV Proteinase Inhibitors" *Science* 248:358–362 (1990).

T. Robins et al., "HIV Protease Inhibitors: Their Anti–HIV Activity and Potential Role in Treatment" *J. Acquired Immune Deficiency Syndromes* 6(2):162–170 (1993).

Communications to the Editor, "Intriguing Structure—Activity Relations Underlie the Potent Inhibition of HIV Protease by Norstatine–Based Peptides" *J. Med. Chem.* 35:1318–1320 (1992).

DIPEPTIDE COMPOUND OR PHARMACEUTICALLY ACCEPTABLE SALT THEREOF AND MEDICAL USE THEREOF

FIELD OF THE INVENTION

The present invention relates to a novel dipeptide compound having inhibitory action against the enzymatic activity of a protease derived from HIV virus. More specifically, it relates to a novel dipeptide compound having an acyl group of a monocyclic carboxylic acid which links to an amino group of the N-terminal of the dipeptide.

In addition, the present invention relates to a medicinal use in which the inhibitory action of a novel dipeptide compound against a protease derived from HIV virus suppresses the proliferation of HIV virus in vivo.

BACKGROUND OF THE INVENTION

Human immunodeficiency virus (hereinafter referred to HIV) which causes AIDS produces a precursor protein comprising Gag protein used for the formation of the said virus particles and reverse transcriptase in host cells. This precursor protein is cleaved by a protease (hereinafter referred to HIV protease) derived from the virus into a specific size to perform its function. Therefore, a HIV protease inhibitor exhibits antiviral activity by inhibiting an enzymatic activity of HIV protease to block the formation and maturation of infectious virus particles. Several kinds of HIV protease inhibitors have been already reported, comprising synthetic peptide-like compound called transition-state mimetics (T. Robins, J. Plattner, J. Acquir. Immun. Defic. Syndr. 6, 162 (1993)). Hydroxyethylamine type derivatives such as Ro 31-8959 comprising phenylalanine ψ[CH(OH)CH$_2$N] decahydroisoquinoline carboxylic acid skeleton similar to the amino acid sequence -Tyr . . . Pro- or -Phe . . . Pro- as a cleavage site of the HIV protease (N. A. Roberts et al., Science 248, 358–361 (1990)) and hydroxymethylcarboxamide type derivatives such as peptide derivatives comprising a norstatine skeleton phenylalanine ψ[CH(OH)C(O)N) proline were reported to be useful as a HIV protease inhibitor (T. F. Tam et al., J. Med. Chem. 35, 1318–1320 (1992)).

The present inventors also found that a group of synthetic peptides which were transition-state mimetics comprising 3-amino-2-hydroxy-4-phenylbutanoyl residues as the skeletal structure thereof strongly inhibited HIV protease activity to be useful as an anti-AIDS agents and proposed them as HIV protease inhibitors (Japanese laid-open patent No. 170722/1993).

These transition-state mimetics are considered as the most promising anti-AIDS agents of the next generation following reverse transcriptase inhibitors of nucleic acid derivatives, such as AZT (azide thymidine), DDC (dideoxycytidine), DDI (dideoxyinosine). These are already used clinically as anti-AIDS agents and clinical use, clinical tests and researches thereof are in progress. That is, clinical application of HIV protease inhibitors has been tried to suppress the formation of virus particles in host cell and prevent the proliferation and infection of HIV, resulting in the prevention of onset of AIDS (Nakajima et al., Gekkan-Yakuji, vol. 35, 2983–2989 (1993)).

However, among these peptide-like compounds, conventional-type compounds belonging to hydroxymethylcarboxamide derivatives exhibiting excellent HIV protease inhibitory activity have a hydrophobic acyl group at the N-terminal amino group of the tripeptide chain. Therefore, in many cases, problems, such as, (1) their insolubility in water, (2) instability in vivo and, (3) low oral absorptivity have been reported (Hiroaki Mitsuya, Kagaku, vol. 64, No. 7, p462–470 (1994)). Since anti-AIDS agents are consecutively administered for long durations, development of compounds with higher bioavailability, that is, easily absorbed and stable in vivo, especially in the case of oral administration has been desired. Development of a peptide compound with excellent HIV protease inhibitory activity which has a low molecular weight and is resistant against degradation by various kinds of digestive enzymes or proteolytic enzymes, is desired. More specifically development of a novel peptide compound with a small size of acyl group linked to the N-terminal amino group which comprises only low molecular weight dipeptide-structure as transition-state mimetics is desired.

An object of the present invention is to provide a novel dipeptide compound which has nearly the same anti-HIV protease inhibitory activity as that of a transition-state mimetic peptide compound having a tripeptide chain and has a lower molecular weight. The object of the present invention is to provide a novel dipeptide compound which is different from various types of hydroxymethylcarboxamide tripeptide compounds designed as conventional HIV protease inhibitors with respect to peptide chain length and exhibit excellent HIV protease inhibitory activity or suppressive action on the proliferation of HIV virus. Another object of the present invention is to provide a suppressive agent against HIV virus proliferation comprising a novel dipeptide compound as an effective ingredient.

The present inventors studied eagerly to design and prepare a novel dipeptide compound which has a clearly different structure from that of a conventional hydroxymethylcarboxamide-type peptide compound. The present inventors investigated whether or not these dipeptide compounds have a HIV protease inhibitory activity as designed and found that they exhibited excellent activities and accomplished the present invention.

SUMMARY OF THE INVENTION

Accordingly, the present invention is to provide a novel dipeptide compound having a chemical structure described as the following items (1)–(6) and a suppressive action on HIV virus proliferation in vivo.

(1) A novel dipeptide compound represented in General formula (I) or a pharmaceutically acceptable salt thereof. General formula (I)

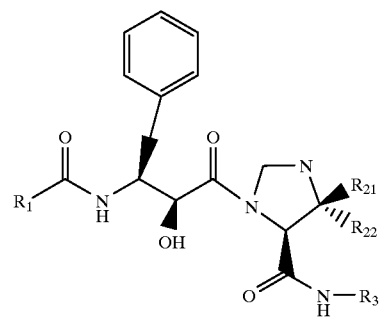

(wherein R$_1$ represents 5-membered or 6-membered monocyclic hydrocarbon group, or heterocyclic group wherein more than one of carbon atom in said monocyclic hydrocarbon can be substituted by hetero atoms comprising 3 or less substituted group in said cyclic group, X represents a methylene group (—CH$_2$—), a chloromethylene group (—CH(Cl)—), an oxygen atom, a sulfur atom or sulfonyl group (—SO$_2$—), R$_{21}$ and R$_{22}$ each represent a hydrogen atom or an aliphatic hydrocarbon having 1–6 carbons which can be linear or branched. R$_3$ represents an aliphatic hydrocarbon group having 1–6 carbons which can be linear or branched or a monovalent group derived from an aromatic monocyclic hydrocarbon wherein the sum of carbon number thereof is 12 or less, and halogen atoms can be substituted in aromatic ring of said aromatic monocyclic hydrocarbon group.)

(2) A novel dipeptide compound represented in General Formula II or a pharmaceutically acceptable salt thereof.

General formula II

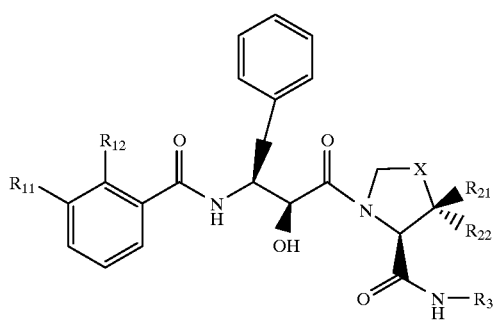

(II)

wherein X, R$_{21}$, R$_{22}$ and R$_3$ represent the same group as that in the above general formula (I), respectively.

R$_{11}$ represents a hydrogen atom, an amino group or a hydroxy group.

R$_{12}$ represents a hydrogen atom or aliphatic hydrocarbon group having 1–4 carbons which can be linear or branched.)

(3) A novel dipeptide compound represented in General formula (III) or a pharmaceutically acceptable salt.

General formula III

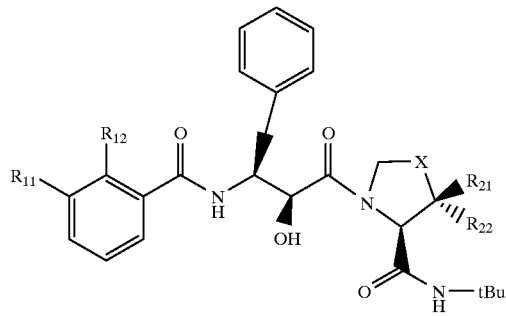

(III)

(wherein X, R$_{21}$ and R$_{22}$ represents the same group as that in the above general formula (I), and R$_{11}$ and R$_{12}$ represents the same group as that in the above general formula (II).

(4) A novel dipeptide compound represented in General formula (IV) or a pharmaceutically acceptable salt thereof.

General formula IV

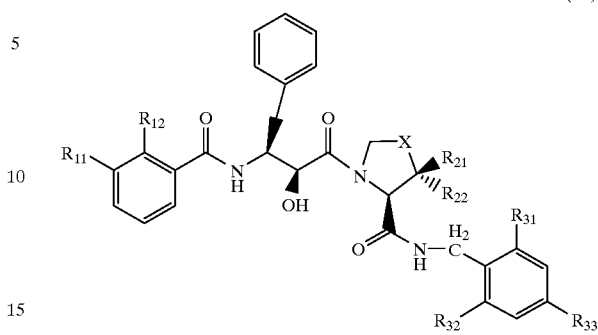

(IV)

(wherein X, R$_{21}$ and R$_{22}$ represents the same group as that in the above general formula (I), and R$_{11}$ and R$_{12}$ represents the same group as those in the above general formula (II).

R$_{31}$, R$_{32}$ and R$_{33}$ each represents a hydrogen atom, a halogen atom or an aliphatic hydrocarbon having 1–4 carbons which can be linear or branched.) (5) A novel dipeptide compound represented in General Formula V or a pharmaceutically acceptable salt thereof.

General formula V

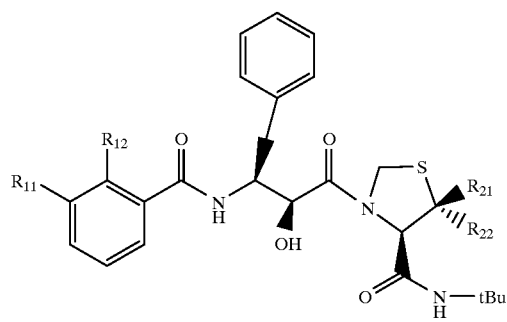

(V)

(wherein R$_{11}$ represents an amino group or a hydroxy group. R$_{12}$ represents a methyl group or an ethyl group.

R$_{21}$ and R$_{22}$ each represents a hydrogen atom or a methyl group.)

(6) A novel dipeptide compound represented in General Formula VI or a pharmaceutically acceptable salt thereof.

General formula VI

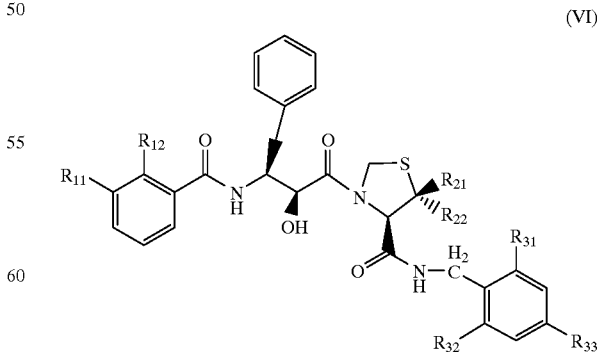

(VI)

(wherein R$_{11}$ represents an amino group or a hydroxy group. R$_{12}$ represents a hydrogen atom, a methyl group or an ethyl group.

$R_{21}$ and $R_{22}$ each represents a hydrogen atom or a methyl group.

$R_{31}$, $R_{32}$ and $R_{33}$ each represents a halogen atom or a methyl group.)

Further, the present invention is to provide an anti-AIDS agent comprising a novel dipeptide compound described in the above items (1)–(6) or a pharmaceutically acceptable salt thereof as an effective ingredient.

DETAILED DESCRIPTION OF THE INVENTION AND PREFERRED EMBODIMENTS

The dipeptide compound of the present invention comprises α-aminocarboxamide including cyclic group linked to 3-amino-2 hydroxy-4-phenylbutanoyl residue as transition-state mimetic essential for HIV protease inhibitory activity through an amide bond and can be clarified as a hydroxymethylcarboxamide derivative.

In the dipeptide compound of the present invention, the steric configuration of 3-amino-2-hydroxy-4-phenylbutanoyl residue skeleton is preferably (2S,3S) epimer and, in α-aminocarboxamide comprising 5-membered cyclic group including X, (L) epimer of corresponding cyclic α-amino acid can be preferably used.

$R_3$ which substitutes N atom carbamoyl group of said α-aminocarboxamide can be an aliphatic hydrocarbon group having 1–6 carbons or a monovalent group derived from an aromatic monocyclic hydrocarbon comprising 12 or less carbon atoms, wherein a hydrocarbon chain in an aliphatic hydrocarbon group or that in an aromatic hydrocarbon group can be linear or branched. Said monovalent group derived from an aromatic monocyclic hydrocarbon comprises both of a group having a binding site in an aromatic monocyclic ring and a group having a binding site in an aromatic side chain. In addition, a halogen atom can substitute a hydrogen on an aromatic cyclic hydrocarbon. That is, said substituted carbamoyl group can be used as far as it can be formed by the reaction of the corresponding carboxy group with the primary amine comprising said $R_3$ group.

An aliphatic hydrocarbon group having 1–6 carbons used in this $R_3$ group can be preferably a methyl, ethyl, propyl, isopropyl, butyl, isobutyl, sec-butyl, tert-butyl, pentyl, hexyl group etc., more preferably a branched alkyl group having 3–5 carbons and, most preferably, a tert-butyl group. On the other hand, as an aromatic monocyclic hydrocarbon group having 12 or less carbons, a phenyl group having a free valence on the ring, hydrocarbon substituted phenyl group having a side chain of chain hydrocarbon group, a benzyl group having a free valence in the side chain and hydrocarbon substituted benzyl group having a side chain in the ring, such as, 2-methylbenzyl group, 2,6-dimethylbenzyl group and 2,4 6-trimethylbenzyl group can be exemplified. Further, as a halogen atom, chlorine atom, bromine atom or fluorine atom can be exemplified and a chlorine atom is preferable. Among these aromatic monocyclic hydrocarbon groups, a benzyl or phenethyl group having a free valence in the side chain or a hydrocarbon substituted benzyl group having a side chain in the ring is preferable, and a hydrocarbon substituted benzyl group having a side chain in the ring is more preferable. Further, a benzyl group or a hydrocarbon substituted benzyl group having a side chain at any of ortho-position such as position 2 or 6 or para-position, that is, position 4, more specifically, 2-methylbenzyl group, 2,6-dimethylbenzyl group or 2,4,6-trimethylbenzyl group is more preferable.

In a hydrocarbon substituted benzyl group having a side chain at any one of position 2,4 or 6 as well as the above benzyl groups, a side chain is preferably a alkyl group having 1–4 carbons. 2-Methylbenzyl group, 2,6-methylbenzyl group or 2,4,6-trimethylbenzyl group is more preferable. Among them, mono or disubstituted benzyl group having one or two alkyl groups with 1–4 carbons especially methyl group, at ortho-position, that is, position 2 or 6 at side chain are preferable. More specifically, 2-methylbenzyl group or 2,6-dimethylbenzyl group is more preferable. In addition, a halogen substituted benzyl group at ortho-position, that is, position 2 or 6, or at para-position, that is, position 4 is preferable and chlorine substituted 2-chlorobenzyl group is more preferable among halogen substituted benzyl groups. Specifically monohalogen or dihalogen substituted benzyl group at one or the both of ortho positions, that is position 2 and 6, especially 2-chlorobenzyl group substituted with a chlorine atom as a halogen atom, is more preferable.

X containing in a 5-membered ring forming said α-aminocarboxamide can be methylene group (—CH$_2$—), chloromethylene group (—CH(Cl)—), oxygen atom or sulfur atom including sulfinyl group or sulfonyl group other than thio group. That is, when both of $R_{21}$ and $R_{22}$ are hydrogen atoms, a corresponding α-amino acid in a 5-membered ring is proline in the case of methylene group (—CH$_2$), 4-chloropyrrolidine-2-carboxylic acid in the case of chloromethylene group, 1,3-oxazolidine-4-carboxylic acid in the case of oxygen atom, 1,3 thiazolidine-4-carboxylic acid in the case of sulfur atom, 1,3-thiazolidine-1,1-dioxide-4-carboxylic acid in the case of sulfonyl group etc. $R_{21}$ and $R_{22}$ in said 5-membered ring can be selected from the group consisting of hydrogen atom and aliphatic hydrocarbon groups having 1–6 carbons, wherein the aliphatic hydrocarbon group can be linear or branched. The $R_{21}$ and $R_{22}$ each group is preferably a hydrogen atom or an alkyl group having 1–4 carbons, more preferably, a hydrogen atom or methyl group.

1,3-Thiazolidine-4-carboxylic acid with sulfur atom as X, 1,3-thiazolidine-1,1-dioxide-4-carboxylic acid with sulfonyl group, 4-chloropyrrolidine-2-carboxylic acid with chloromethyl group or 5,5-dimethyl-1,3-thiazolidine-4-carboxylic acid with hydrogen atom or methyl group as $R_{21}$ and $R_{22}$ is more preferable. Said mono-ring $R_1$ group in a acyl group $R_1$—CO— which substitutes N-terminal amino group in 3-amino-2-hydroxy-4-phenylbutanoyl skeleton and characterizes dipeptide compound of the present invention can be 5-membered ring, 6-membered ring, cyclic hydrocarbon group or heterocyclic group wherein more than one carbon atoms in said cyclic hydrocarbon group can be substituted with heteroatoms. Said heteroatom means nitrogen atom, sulfur atom or oxygen atom and sulfur atom can be sulfinyl group or sulfonyl group other than thio group. Further, carbonyl group wherein one of carbon atoms is substituted with oxo-oxygen can be included.

In addition, said cyclic group $R_1$ can have 3 or less another substituted groups. Said cyclic group $R_1$ can be exemplified as follows:

As 6-membered ring of said cyclic group $R_1$, phenyl group as a cyclic aromatic group, 4-pyridyl group, 2-pyridyl group, 3-pyridyl group, 2-pyrimidinyl group, 4-pyrimidinyl group, 5-pyrimidinyl group as a corresponding nitrogen substituted hetero aromatic group, cyclohexyl group as a cycloaliphatic group, 4-piperidinyl group or 2-morpholinyl group as a corresponding heterocyclic and cyclic group of the above 6-membered ring substituted with 3 or less substituted group such as an alkyl group having 1–6 carbons, carboxyl group, carbamoyl group, hydroxyl group, amino group, nitro group, alkylamino group or alkoxy carbonyl group etc. can be exemplified. As specific examples, tolyl group, xylyl group, cumenyl group or mesityl group as a phenyl group substituted with 1–3 alkyl groups having 1–6 carbons, 4-carboxyphenyl group, 2-carboxyphenyl group or 3-carboxyphenyl group as a phenyl group substituted with carboxyl group, 4-carbamoyl phenyl group, 2-carbamoyl phenyl group or 3-carbamoyl phenyl group as a phenyl group substituted with carbamoyl group, 4-hydroxyphenyl group, 2-hydroxyphenyl group, 3-hydroxyphenyl group, 3-hydroxy-2-methylphenyl group or 2-ethyl-3-hydroxyphenyl group as a phenyl group substituted with hydroxy group, 4-aminophenyl group, 2-aminophenyl group or 3-aminophenyl group as a phenyl group substituted with amino group, 3,5-dinitro-phenyl group as a phenyl group substituted with nitro-group, 3-methylaminophenyl group as a phenyl group substituted with alkylamino group, 4-methoxycarbonylphenyl group, 2-methoxycarbonylphenyl group or 3-methoxycarbonylphenyl group as a phenyl group substituted with alkoxycarbonyl group etc. can be exemplified.

As 5-membered ring of said cyclic group $R_1$, heterocyclic aromatic group such as 2-furyl group, 3-furyl group, 2-thienyl group, 2-pyrrolyl, 3-pyrrolyl etc. or cyclic aliphatic group such as cyclopentyl group, 2-cyclopentene-1-yl group etc., the corresponding heterocyclic group such as pyrrolidine-2-yl group, pyrroline-2-yl group, 2-tetrahydrofuryl group, 2-tetrahydrothienyl group etc., or cyclic group of the above 5-membered ring substituted with 3 or less substituted groups such as alkyl group having 1–6 carbons, carboxy group, carbamoyl group, hydroxy group, amino group, nitro group, alkyl amino group, alkoxycarbonyl group etc. can be exemplified.

Said cyclic group $R_1$ in the peptide compounds of the present invention is preferably cyclic aromatic group or heterocyclic aromatic group having 3 or less substituted groups. 6-Membered ring cyclic aromatic group or heterocyclic aromatic group is more preferable. Among them, phenyl group substituted with 1 or 2 substituted groups at position 2 and position 3 in the phenyl group is more preferable, specifically, disubstituted phenyl group represented in the following general formula (VII) is more preferable:

General formula VII

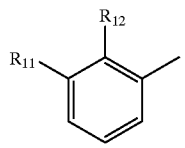

(VII)

(wherein $R_{11}$ represents amino group or hydroxy group, $R_{12}$ represents aliphatic hydrocarbon group having 1–4 carbons which can be linear or branched). Further, $R_{11}$ in disubstituted phenyl group and $R_{12}$ are more preferably hydroxy group and methyl group or ethyl group.

When at least two of $R_1$, $R_2$ and X of the dipepetide compound of the present invention are selected from preferable groups, it can be more preferable dipeptide compound. For example, dipeptide substituted with disubstituted phenyl group represented in the above general formula (VII) to $R_1$ and with tert-butyl group to $R_3$, that is, dipeptide represented in the following general formula (III) can be more preferable:

General formula III

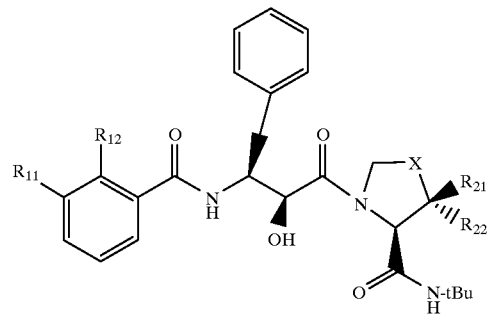

(III)

(wherein X represents the same as X in the general formula (I). $R_{11}$ represents amino group or hydroxy group and $R_{12}$ represents aliphatic hydrocarbon group having 1–4 carbons which can be linear or branched. $R_{21}$ and $R_{22}$ each represents hydrogen atom or aliphatic hydrocarbon group having 1–6 carbons which can be linear or branched.

Or dipeptide wherein $R_1$ is disubstituted phenyl group represented in the above general formula (VII) and $R_3$ hydrocarbon substituted benzyl group with a side chain at any one of ortho-position, that is, position 2 or 6 or at para-position, that is, position 4, or benzyl group or hydrocarbon substituted benzyl group substituted further with halogen atom at orthoposition, that is, position 2 or 6, or at para-position 4, represented in the following general formula (VIII) with hydrocarbon substituted benzyl group having at most 12 carbons can be preferable:

General formula VIII

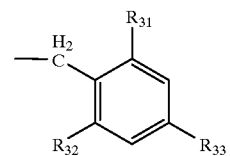

(VIII)

(wherein $R_{31}$, $R_{32}$, and $R_{33}$ each represents hydrogen atom, halogen atom or aliphatic hydrocarbon group having 1–4 carbons which can be linear or branched)

That is, dipeptide compound represented in the following general formula (IV) can be more preferable. Chlorine atom as halogen atom is more preferable.

General formula IV

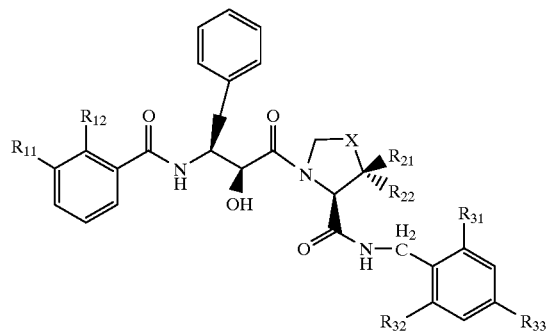

(IV)

(wherein X represents the same as X represented in the above general formula (I). $R_{11}$ represents amino group or hydroxyl group and $R_{12}$ represents aliphatic hydrocarbon group having 1–4 carbons which can be linear or branched.

$R_{21}$ and $R_{22}$ each represents hydrogen atom or aliphatic hydrocarbon group having 1–6 carbons which can be linear or branched. $R_{31}$, $R_{32}$ and $R_{33}$ each represents hydrogen atom, halogen atom or aliphatic hydrocarbon group having 1–4 carbons which can be linear or branched.)

A chlorine atom can be selected more preferably as a halogen atom. In the aforementioned general formula (IV), monosubstituted or disubstituted benzyl group at one or the both of ortho positions, that is, position 2 and 6 as a substituted group at C-terminus can be selected more preferablly.

The dipeptide represented in the aforementioned general formula (V) or (VI) which is selected from those with preferable X represented in the above general formula (III) or (IV) is more preferable. As an example of these compounds in the general formula (V) or (VI), (R)-N-tert-butyl-3-[(2S,3S)-2-hydroxy-3-[3-hydroxy-2-methylbenzoyl]amino-4-phenylbutanoyl]-1,3-thiazolindine-4-carboxamide, (R)-N-tert-butyl-3-[(2S,3S)-2-hydroxy-3-[3-amino-2-methylbenzoyl]amino-4-phenylbutanoyl)-1,3-thiazolidine-4-carboxamide, (R)-N-tert-butyl-3-[(2S,3S)-2-hydroxy-3-[2-ethyl-3-hydroxybenzoyl]amino-4-phenylbutanoyl]-1,3-thiazolidine-4-carboxamide, (R)-N-tert-butyl-3-[(2S,3S)-2-hydroxy-3-[3-amino-2-ethylbenzoyl]amino-4-phenylbutanoyl]-1,3-thiazolidine-4-carboxamide, (R)-N-tert-butyl-3-[(2S,3S)-2-hydroxy-3-[3-hydroxy-2-methylbenzoyl]amino-4-phenylbutanoyl]-5,5-dimethyl-1,3-thiazolidine-4-carboxamide, (R)-N-tert-butyl-3-[(2S,3S)-2-hydroxy-3-[3-amino-2-methylbenzoyl]amino-4-phenylbutanoyl]-5,5-dimethyl-1,3-thiazolidine-4-carboxamide, (R)-N-tert-butyl-3-[(2S,3S)-2-hydroxy-3-[2-ethyl-3-hydroxybenzoyl]amino-4-phenylbutanoyl]-5,5-dimethyl-1,3-thiazolidine-4-carboxamide, (R)-N-tert-butyl-3-[(2S,3S)-2-hydroxy-3-[3-amino-2-ethylbenzoyl]amino-4-phenylbutanoyl]-5,5-dimethyl-1,3-thiazolidine-4-carboxamide, (R)-N-(2-methylbenzyl)-3-[(2S,3S)-2-hydroxy-3-[3-hydroxy-2-methylbenzoyl]amino-4-phenylbutanoyl]-1,3-thiazolidine-4-carboxamide, (R)-N-(2-methylbenzyl)-3-[(2S,3S)-2-hydroxy-3-[3-amino-2-methylbenzoyl]amino-4-phenylbutanoyl]-1,3-thiazolidine-4-carboxamide, (R)-N-(2-methylbenzyl)-3-[(2S,3S)-2-hydroxy-3-[2-ethyl-3-hydroxybenzoyl]amino-4-phenylbutanoyl]-1,3-thiazolidine-4-carboxamide, (R)-N-(2-methylbenzyl)-3-[(2S,3S)-2-hydroxy-3-[3-amino-2-ethylbenzoyl]amino-4-phenylbutanoyl]-1,3-thiazolidine-4-carboxamide, (R)-N-(2-methylbenzyl)-3-[(2S,3S)-2-hydroxy-3-[3-hydroxy-2-methylbenzoyl]amino-4-phenylbutanoyl]-5,5-dimethyl-1,3-thiazolidine-4-carboxamide, (R)-N-(2-methylbenzyl)-3-[(2S,3S)-2-hydroxy-3-[3-amino-2-methylbenzoyl]amino-4-phenylbutanoyl]-5,5-dimethyl-1,3-thiazolidine-4-carboxamide, (R)-N-(2-methylbenzyl)-3-[(2S,3S)-2-hydroxy-3-[2-ethyl-3-hydroxybenzoyl]amino-4-phenylbutanoyl]-5,5-dimethyl-1,3-thiazolidine-4-carboxamide, (R)-N-(2-methylbenzyl)-3-[2S,3S)-2-hydroxy-3-[3-amino-2-ethylbenzoyl]amino-4-phenylbutanoyl]-5,5-dimethyl-1,3-thiazolidine-4-carboxamide, (2S,4S)-N-tert-butyl-3-[(2S,3S)-3-(2-ethyl-3-hydroxybenzoyl)amino-2-hydroxy-4-phenylbutanoyl]-4-chloropyrrolidine-2-carboxamide, (R)-N-(2,6-dimethylbenzyl)-3-[(2S,3S)-3-(3-hydroxy-2-methylbenzoyl)amino-2-hydroxy-4-phenylbutanoyl]-1,3-thiazolidine-4-carboxamide, (R)-N-(2-chlorobenzyl)-3-[(2S,3S)-3-(3-hydroxy-2-methylbenzoyl)-amino-2-hydroxy-4-phenylbutanoyl]-5,5-dimethyl-1,3-thiazolidine-4-carboxamide, (R)-N-(2-chlorobenzyl)-3-[(2S,3S)-3-(3-hydroxy-2-methylbenzoyl)-amino-2-hydroxy-4-phenylbutanoyl]-1,3-thiazolidine-4-carboxamide, etc. can be exemplified.

For example, pharmaceutical acceptable salts of the dipeptide compound of the present invention comprise 5–7 membered ring of $R_1$ group in said compound, substituted group therein, or in the case of another 5–7 membered ring having basic nitrogen, salts of said nitrogen with various pharmaceutical acceptable acids, more specifically, pharmaceutically acceptable salts such as hydrochloride salt, acetic acid salt, methanesulfonic acid salt, etc. Pharmaceutically acceptable salts also comprise salts monovalent cation with carboxyl group or phenolic hydroxyl group substituted in $R_1$ group, more specifically, sodium salt or ammonium salt, etc.

A group of dipeptide compounds represented in the above general formula (I) can be prepared by a preparative method described as below. A process of N-acylation will be summarized. A compound represented in the general formula (IX), that is, hydroxymethylcarboxamide type of dipeptide without substitution at N-terminal can be used as an intermediate to yield N-acyl product eventually:

General formula IX

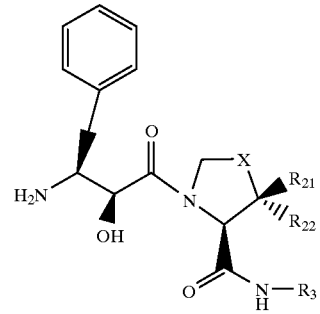

(IX)

(wherein X, $R_3$, $R_{21}$ and $R_{22}$ represents the same as X, $R_3$, $R_{21}$ and $R_{22}$ in the above formula (I) respectively)

A method for preparing N-acyl dipeptide compound represented in the general formula (I).

Process [1] Preparation of intermediate compound represented in the general formula (IX).

It corresponds to the intermediate in the preparation of hydroxymethylcarboxamide type of HIV protease inhibitor which was already reported in various publications. (Yoshiaki Kiso, Yuuki-gosei-kyoukaishi, vol.52, 403–412 (1994) etc.,) For example, condensation of α-aminocarboxamide derivative represented in the following general formula (X):

General formula X

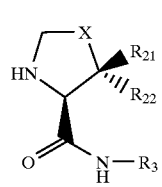

(X)

(wherein X, R₃, R₂₁ and R₂₂ represents the same as X, R₃, R₂₁ and R₂₂ represented in the aforementioned general formula (I)) with N-protected derivative (2S,3S)-3-amino-2-hydroxy-4-phenylbutanoic acid represented in the following general formula (XI):

General formula XI

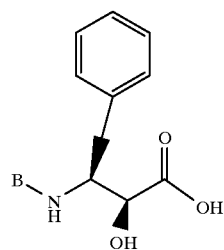

(XI)

(wherein B represents a protective group of amino group which can be deprotected with acid)

Using carbodiimide reagents such as DCC(N,N-dicyclohexyl-carbodiimide), EDC(1-ethyl-3-(3-N,N-dimethylaminopropyl) carbodiimide, etc., and additive compound such as HONB(N-hydroxy-norbornene-2,3-dicarboxyimide), HOBt(N-hydroxybenztriazole), to form peptide bond yields the N-protected derivatives of dipeptide represented in the general formula (XII):

General formula XII

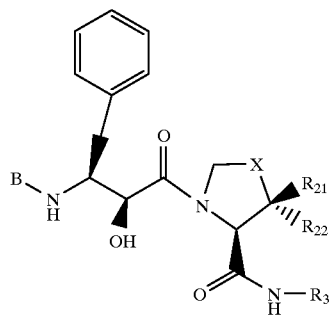

(XII)

(wherein B represents the same as B in the general formula (XI) and X, R₃, R₂₁ and R₂₂ represents the same as X, R₃, R₂₁ and R₂₂ in the general formula (I)) respectively.)

In the next step, said N-protected dipeptide can be deprotected with acid, for example, hydrochloric acid in dioxane to give an intermediate of hydroxymethylcarboxamide type of dipeptide represented in the general formula (IX). B as a protective group of amino group is preferably a protective group used widely in protection of α-amino group in peptide synthesis such as tert-butyloxycarbonyl group.

Process [2] N-acylation

Reaction of carboxylic acid represented in the general formula (XIII):

General formula XIII

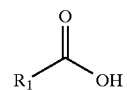

(XIII)

(wherein R₁ represents the same as R₁ in the aforementioned general formula (I).)

With a carbodiimide reagent such as EDC and additive compound such as HOBt to give an active ester of said carboxylic acid, or with acid chloride of chloro-formate such as isobutyl chloroformate etc., to give mixed acid anhydride. That is, said carboxylic acid is converted first to preactivated derivatives represented in the following general formula (XIV) wherein Y comes from said additive compound or acid chloride:

General formula XIV

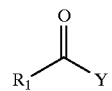

(XIV)

(wherein R₁ represents the same as R₁ in the aforementioned general formula(I).)

Reaction of said carboxylic acid derivative represented in the general formula (IX) with an intermediate represented in the aforementioned general formula (XIV) in a solvent such as N,N-dimethylformamide etc. gives desired acylated hydroxymethylcarboxamide type derivative represented in the general formula (I).

When carbodiimide reagent is used, activation of said carboxylic acid and N-acylation thereof can be naturally carried out in the same reaction mixture and at the same time. In a N-acylation using these acid anhydride, if unnecessary side reaction occurs on substituted group present in R₁ group such as amino group, hydroxyl group, carboxyl group, etc., it is quite natural that the reaction can be carried out after protection with widely used protective group followed by deprotection.

Hydroxymethylcarboxamide type derivative prepared according to the above process represented in the general formula (I) can be purified by recrystallization and/or column chromatography etc., if necessary, and be used as a HIV protease inhibitor.

Since the dipeptide compound of the present invention is prepared from an intermediate represented in the general formula (IX) and an activated derivative of carboxylic acid represented in the general formula (XIV), identification of the molecular structure thereof can be easily performed by any one of conventional spectrophotometry such as nuclear magnetic resonance and/or infrared absorption spectrometry and/or by conventional fragment analysis of mass spectroscopy referring to the molecular structure of the original raw material.

The dipeptide compound of the present invention comprises α-aminocarboxamide including cyclic group linked through an amide bond to 3-amino-2-hydroxy-4-phenylbutanoyl residue as a transition-state mimetic which is essential for HIV protease inhibitory activity and can be clarified as hydroxymethylcarboxamide type derivative which is already reported and can be HIV protease inhibitor as tripeptide compound. That is, as described later in the example, the compound exhibit an anti-viral activity by blocking formation and maturation of infectious HIV virus particles in T lymphocyte using HIV protease inhibitory activity thereof. Accordingly, it has a medicinal use as an anti-AIDS agent through its suppressive effect on formation and maturation of infections virus particles.

On the clinical application of the dipeptide compound of the present invention, it can be administered according to conventional method as a pharmaceutical using conventional carriers and fillers. Generally, dipeptide compound of the present invention can be administered intravenously or intramuscularly as injection preparations, parenterally as sprays or suppositories or orally as granules, capsules or tablets according to conventional methods. Bioavailability of the dipeptide compound of the present invention is excellent through digestive tracts, and therefore, oral administration as granules or capsules wherein said compound is kept solid is quite suitable. The administration dosage is determined by considering symptoms of patients, therapeutical object such as to prevent onset of AIDS or to suppress progress of AIDS, age, sex etc., and, usually, 10 mg–1 g for an adult with 1–4 times per day. As oral administration preparation, any pharmaceutical preparation applicable to oral administration of various synthetic peptide which was already proposed as HIV protease inhibitor can be applied (Japanese laid-open unexamined patent, No. 170722/1993, etc.).

The novel dipeptide compound and pharmaceutically acceptable salt thereof of the present invention has an advantage such as good absorption through digestive tracts and decrease of biliary excretion due to its dipeptidyl structure of lower molecular weight, wherein acyl group bind directly with N-terminal amino group of dipeptide skeletal part essential for HIV protease inhibitory activity, in addition to its specific and high HIV protease inhibitory activity. Accordingly, it has an advantage to decrease oral dosage necessary for reaching expecting blood concentration level of said peptide-like compound as an effective ingredient to yield pharmaceutical effect on its clinical application as oral anti-AIDS agent. In addition, the peptide compound of the present invention is not only a low molecular weight compound but also peptide-mimic compound without peptide bond of natural amino acids which is excellent for the stability in vivo. The dipeptide of the present invention and the method thereof will be explained more specifically as described below. In addition, characteristics of the dipeptide compound of the present invention suitable for medicinal application such as high HIV protease inhibitory activity, that is, excellent anti-HIV activity, low cytotoxicity will be also exhibited.

In the examples described below, intermediates such as (2S,3S)-H-AHPBA-Pro-NH-tBu(1-[(2S,3S)-3-amino-2-hydroxy-4-phenylbutanoyl]-N'-tert-butyl-L-prolinamide), (2S,3S)-H-AHPBA-Thz-NH-tBu((R)-3-[(2S,3S)-3-amino-2-hydroxy-4-phenylbutanoyl]-1,3-thiazolidine-4-N'-tert-butylcarboxamide), (2S,3S)-H-AHPBA-Dmt-NH-tBu((R)-3-[(2S,3S)-3-amino-2-hydroxy-4-phenylbutanoyl]-5,5-dimethyl-1,3 thiazolidine-4-N'-tert-butylcarboxamide were prepared from (2S,3S)-H-AHPBA((2S,3S) -3-amino-2-hydroxy-4-phenylbutanoic acid, Pro(L-proline), Thz((R)-1,3-thiazolidine-4-carboxylic acid), Dmt ((R)-5,5-dimethyl-1,3-thiazolidine-4-carboxylic acid), NH$_2$-tBu (tert-butylamine) etc., as N-protected derivatives of said dipeptide beforehand according to method which were already reported in publications, followed by deprotection of amino group.

EXAMPLE 1

(R)-N-tert-butyl-3-[(2S,3S)-2-hydroxy-3-[benzoyl] amino-4-phenyl-butanoyl]-1,3-thiazolidine-4-carboxamide To a suspension of (2S,3S)-H-AHPBA-Thz-NH-tBu (365 mg) and benzoic acid (122 mg) in DMF (3 ml), EDC.HCl (1 ethyl-3-(3-N,N -dimethylamino-propyl)carbodiimide hydrochloride salt (192 mg) and HOBt.H$_2$O (N-hydroxybenzotriazole/153 mg) were added, which was stirred for 14 hours at room temperature. The reaction mixture was concentrated under reduced pressure to give residue containing product. The product was purified and recovered from the obtained residue by the operation described below. The obtained residue was dissolved in 25 ml of ethyl acetate, which was washed with 10% citric acid aqueous solution, 5% sodium bicarbonate aqueous solution and saturated brine solution consecutively and dried over magnesium sulphate anhydride. The residue obtained by concentration under reduced pressure was purified by silica gel chromatography (dichloromethane/methanol), followed by recrystallization from ethyl acetate/n-hexane to yield purified the above-mentioned compound (296 mg). The HPLC retention time of said compound under the conditions described below was 19.55 min. and the molecular weight was found to be 469 by time of flight mass spectrometry, so that it was identified as the desired compound.

HPLC retention time: 19.55 min.

HPLC conditions

Column: YMC AM302 column, φ 4.6×150 mm

Elution vehicle: 0.1% TFA (trifluoroacetic acid)/H$_2$0–CH$_3$CN

Elution conditions: 0%–100%, gradient; 30 min.

Flow rate: 1 ml/min.

TOF-MASS (time of flight mass spectrometry): [M+H]+ 470

EXAMPLE 2

(R)-N-tert-butyl-3-[(2S,3S)-2-hydroxy-3-[2-methylbenzoyl]amino-4-phenylbutanoyl]-1,3-thiazolidine-4-carboxamide To a suspension of (2S,3S)-H-AHPBA-Thz-NH-tBu (365 mg) and o-toluic acid (136 mg) in DMF (3 ml), EDC.HCl (192 mg) and HOBt.H$_2$O (153 mg) were added, which was stirred for 14 hours at room temperature. The reaction mixture was concentrated under reduced pressure to give residue containing product. The above-mentioned product (295 mg) was obtained by the same purification as described in example 1. Said compound was identified as the desired compound by HPLC analysis and time of flight mass spectrometry.

HPLC retention time: 19.95 min. (The conditions were the same as those in example 1.)

TOF-MASS: [M+H]+484

EXAMPLE 3

(R)-N-tert-butyl-3-[(2S,3S)-2-hydroxy-3-[3-methylbenzoyl]amino-4-phenylbutanoyl]-1,3-thiazolidine-4-carboxamide To a suspension of (2S,3S)-H-AHPBA-Thz-NH-tBu (365 mg) and m-toluic acid (136 mg) in DMF (3 ml), EDC.HCl (192 mg) and HOBt.H$_2$O (153 mg) were added, which was stirred for 14 hours at room temperature. The reaction mixture was concentrated under reduced pressure to give residue containing product. The above-mentioned product (406 mg) was obtained by the same purification as described in example 1. Said compound was identified as the desired compound by HPLC analysis and time of flight mass spectrometry.

HPLC retention time: 20.36 min. (The conditions were the same as those in example 1.)
TOF-MASS: (M+H]+484

EXAMPLE 4

(R)-N-tert-butyl-3-[(2S,3S)-2-hydroxy-3-[4-methylbenzoyl]amino-4-phenylbutanoyl]-1,3-thiazolidine-4-carboxamide To a suspension of (2S,3S)-H-AHPBA-Thz-NH-tBu (365 mg) and p-toluic acid(136 mg) in DMF(3 ml), EDC.HCl (192 mg) and HOBt.H$_2$O (153 mg) were added, which was stirred for 14 hours at room temperature. The reaction mixture was concentrated under reduced pressure to give residue containing product. The above-mentioned product (406 mg) was obtained by the same purification as the described in example 1. Said compound was identified as desired compound by HPLC analysis and time of flight mass spectrometry.

HPLC retention time: 20.27 min. (The conditions were the same as those in example 1.)
TOF-MASS: [M+H]+484

EXAMPLE 5

(R)-N-tert-butyl-3-[(2S,3S)-2-hydroxy-3-[2-hydroxybenzoyl]amino-4 -phenylbutanoyl]-1,3-thiazolidine-4-carboxamide To a suspension of (2S,3S)-H-AHPBA-Thz-NH-tBu (365 mg) and salicylic acid (138 mg) in DMF (3 ml), EDC.HCl (192 mg) and U HOBt.H$_2$O (153 mg) were added, which was stirred for 14 hours at room temperature. The reaction mixture was concentrated under reduced pressure to give residue containing product. The above-mentioned product (202 mg) was obtained by the same purification as described in example 1. Said compound was identified as the desired compound by HPLC analysis and time of flight mass spectrometry.

HPLC retention time: 23.89 min. (The conditions were the same as those in example 1.)
TOF-MASS: [M+H]+486

EXAMPLE 6

(R)-N-tert-butyl-3-[(2S,3S)-2-hydroxy-3-[3-hydroxybenzoyl]amino-4-phenylbutanoyl]-1,3-thiazolidine-4-carboxamide To a suspension of (2S,3S)-H-AHPBA-Thz-NH-tBu (365 mg) and m-hydroxybenzoic acid (138 mg) in DMF (3 ml), EDC.HCl (192 mg) and HOBt.H$_2$O (153 mg) were added, which was stirred for 14 hours at room temperature. The reaction mixture was concentrated under reduced pressure to give residue containing product. The above-mentioned product (418 mg) was obtained by the same purification as described in example 1. Said compound was identified as the desired compound by HPLC analysis and flight time type mass spectrometry.

HPLC retention time: 20.69 min. (The conditions were the same as those in example 1.)
TOF-MASS: [M+H]+486

EXAMPLE 7

(R) -N-tert-butyl-3-[(2S,3S)-2-hydroxy-3-[4-hydroxybenzoyl]amino-4-phenylbutanoyl)]-1,3-thiazolidine-4-carboxamide To a suspension of (2S,3S)-H-AHPBA-Thz-NH-tBu (365 mg) and p-hydroxybenzoic acid (138 mg) in DMF(3 ml), EDC.HCl (192 mg) and HOBt.H$_2$O (153 mg) were added, which was stirred for 14 hours at room temperature. The reaction mixture was concentrated under reduced pressure to give residue containing product. The above-mentioned product (392 mg) was obtained by the same purification as described in example 1. Said compound was identified as the desired compound by HPLC analysis and time of flight mass spectrometry.

HPLC retention time: 20.35 min.(The conditions were the same as those in example 1.) TOF-MASS: [M+H]+486

EXAMPLE 8

(R)-N-tert-butyl-3-[(2S,3S)-2-hydroxy-3-[2-aminobenzoyl]amino-4-phenylbutanoyl]-1,3-thiazolidine-4-carboxamide To a suspension of (2S,3S)-H-AHPBA-Thz-NH-tBu (365 mg), 2-(t-butyloxycarbonylamino) benzoic acid (237 mg) and HOBt (135 mg,) in DMF (3 ml), EDC.HCl (210 mg) was added, which was stirred for 14 hours at room temperature. To the reaction mixture, dichloromethane and 3% sodium carbonate aqueous solution were admixed and the organic layer was collected. Then, t-butyloxycarbonyl group was deprotected and the product was recovered as described below. The collected organic layer was washed 3% sodium carbonate aqueous solution, 1N-HCl (twice) and 5% brine solution consecutively and dried over magnesium sulphate anhydride. Magnesium sulphate was removed by filtration, followed by evaporation of solvent. To the residue, dichloromethane (5 ml) and 4N HCl/dioxane solution (5 ml) were added, which was stirred for another 1 hour at room temperature.

The reaction mixture was washed with water, 3% sodium carbonate aqueous solution, 5% brine solution and dried over magnesium sulphate anhydride, and again, concentrated under reduced pressure. The obtained residue was further purified by silica gel chromatography (dichloromethane/methanol). The above-mentioned product (184 mg) was obtained. Said compound was identified as the desired compound by time of flight mass spectrometry.

TOF-MASS: [M+H]+485

EXAMPLE 9

(R)-N-tert-butyl-3-[(2S,3S)-2-hydroxy-3-[3-aminobenzoyl]amino-4-phenylbutanoyl]-1,3-thiazolidine-4-carboxamide To a suspension of (2S,3S)-H-AHPBA-Thz-NH-tBu (365 mg), 3-(t-butyloxycarbonylamino) benzoic acid (237 mg) and HOBt (135 mg) in DMF (3 ml), EDC.HCl (210 mg) was added, which was stirred for 14 hours at room temperature. To the reaction mixture, dichloromethane and 3% sodium carbonate aqueous solution were admixed and the organic layer was collected. Then, deprotection of t-butyloxycarbonyl group, purification were carried out in the same manner as described in example 8. The above-mentioned product (74 mg) was obtained. Said compound was identified as the desired compound by time of flight mass spectrometry.

TOF-MASS: [M+H]+485

EXAMPLE 10

(R)-N-tert-butyl-3-[(2S,3S)-2-hydroxy-3-[4-aminobenzoyl]amino-4-phenylbutanoyl]-1,3-thiazolidine-4-carboxamide To a suspension of (2S,3S)-H-AHPBA-Thz-NH-tBu (365 mg) and 4-(t-butyloxycarbonylamino) benzoic acid (237 mg) and HOBt (135 mg) in DMF (3 ml), EDC.HCl (210 mg) was added, which was stirred for 14 hours at room temperature. To the reaction mixture, dichloromethane and 3% sodium carbonate aqueous solution were admixed and the organic layer was collected. The collected organic layer was washed 3% sodium carbonate aqueous solution, 1N-HCl (twice) and 5% brine solution consecutively and dried over magnesium sulphate anhydrides. Magnesium sulphate was removed by filtration, followed by evaporation of solvent. To the residue, dichloromethane (5 ml) and 4N HCl/dioxane solution (5 ml) were added, which was stirred for 1 hour at room temperature. Then, to the reaction mixture, water was admixed and the water layer was collected for deprotected product to be recovered. The water layer was adjusted by adding sodium carbonate at pH 8–9 and extracted with dichloromethane. The organic layer obtained was washed with 5% brine solution and dried over magnesium sulphate anhydride and again, concentrated under reduced pressure. The obtained residue was further purified by silica gel chromatography (dichloromethane/methanol), followed by recrystallization from ethyl acetate/n-hexane. The above-mentioned product (330 mg) was obtained. Said compound was identified as the desired compound by time of flight mass spectrometry.

TOF-MASS: [M+H]+485

EXAMPLE 11

(R)-N-tert-butyl-3-[(2S,3S)-2-hydroxy-3-[2-carboxybenzoyl]amino-4-phenylbutanoyl]-1,3-thiazolidine-4-carboxamide To a suspension of (2S,3S)-H-AHPBA-Thz-NH-tBu (365 mg) and phthalic anhydride (146 mg) in DMF (3 ml), pyridine (0.5 ml) was added, which was stirred for 14 hours at room temperature, followed by concentration under reduced pressure. The obtained residue was dissolved in ethyl acetate (25 ml). This solution was washed with 10% citric acid aqueous solution and saturated brine solution and dried over magnesium sulphate anhydride, followed by concentration under reduced pressure. The obtained residue was further purified by silica gel chromatography (dichloromethane/methanol), followed by recrystallization from ethyl acetate/n-hexane. The above-mentioned product (498 mg) was recovered. Said compound was identified as the desired compound by HPLC analysis and time of flight mass spectrometry.

HPLC retention time: 17.96 min. (The conditions were the same as those in example 1.)

TOF-MASS: [M+H]+514

EXAMPLE 12

(R) -N-tert-butyl-3-[(2S,3S)-2-hydroxy-3-[3-carboxybenzoyl] amino-4-phenylbutanoyl]-1,3-thiazolidine-4-carboxamide To a suspension of (2S,3S)-H-AHPBA-Thz-NH-tBu (365 mg) and isophtalic acid (166 mg) in DMF (3 ml), EDC.HCl (192 mg) arid HOBt.H$_2$O (153 mg) were added, which was stirred for 14 hours at room temperature, followed by concentration under reduced pressure. The obtained residue was dissolved in ethyl acetate (25 ml). This solution was washed with 10% citric acid aqueous solution and saturated brine solution and dried over magnesium sulphate anhydride, followed by concentration under reduced pressure. The obtained residue was further purified by preparative HPLC. The above-mentioned product was obtained. Said compound was identified as the desired compound by HPLC analysis and time of flight mass spectrometry.

Preparative HPLC conditions

Column: YMC-Pack ODS, φ20×250 mm

Elution vehicle: 0.1% TFA H$_2$O—CH$_3$CN

Elution conditions: 0%–50% gradient; 60 min., thereafter 50% isocratic

Flow rate: 5 ml/min.

Elution time: 67–70 min.

HPLC retention time: 17.96 min.(The conditions were the same as those in example 1.)

TOF-MASS: (M+H]+514

EXAMPLE 13

(R)-N-tert-butyl-3-[(2S,3S)-2-hydroxy-3-[4-carboxybenzoyl]amino-4-phenylbutanoyl]-1,3-thiazolidine-4-carboxamide To a suspension of (2S,3S)-H-AHPBA-Thz-NH-tBu (365 mg) and mono-methyl terephtalate (180 mg) in DMF (3 ml), EDC.HCl (192 mg) and HCBt.H$_2$O (153 mg) were added, which was stirred for 14 hours at room temperature, followed by concentration under reduced pressure. The obtained residue was dissolved in ethyl acetate (25 ml). This solution was washed with 10% citric acid aqueous solution, 5% sodium carbonate aqueous solution and saturated brine solution consecutively and dried over magnesium sulphate anhydride, followed by concentration under reduced pressure. The obtained residue was further purified by silica gel chromatography (dichloromethane/methanol) to give methyl ester of the above-mentioned compound (289 mg), which was dissolved in methanol (5 ml) and stirred for 1 hour at room temperature after the addition of 1N-sodium hydroxide aqueous solution (5 ml). After ester hydrolysis, the reaction mixture was adjusted to pH about 3 by adding conc. hydrochloride and extracted with dichloromethane. Organic layer was dried over sodium sulphate anhydride and concentrated under reduced pressure. The obtained residue was recrystallized from ethyl acetate/n-hexane. The above-mentioned product (220 mg) was obtained. Said compound was identified as the desired compound by HPLC analysis and time of flight mass spectrometry.

HPLC retention time: 20.35 min. (The conditions were the same as those in example 1.)

TOF-MASS: [M+H]+514

EXAMPLE 14

(R)-N-tert-butyl-3-[(2S,3S)-2-hydroxy-3-[2-pyridylcarbonyl]amino-4-phenylbutanoyl]-1,3-thiazolidine-4-carboxamide To a suspension of (2S,3S)-H-AHPBA-Thz-NH-tBu (365 mg) and picolinic acid (123 mg) in DMF (3 ml), EDC.HCl (192 mg) and HOBt.H$_2$O (153 mg) were added, which was stirred for 14 hours at room temperature, followed by concentration under reduced pressure to give residue containing product. The obtained residue was dissolved in ethyl acetate (25 ml). This solution was washed with 5% sodium bicarbonate aqueous solution and saturated brine solution and dried over magnesium sulphate anhydride, followed by concentration under reduced pressure. The obtained residue was further purified by silica gel chromatography (dichloromethane/ methanol), followed by recrystallization from ethyl acetate/n-hexane. The above-mentioned product (364 mg) was obtained. Said compound was identified as the desired compound by HPLC analysis and time of flight mass spectrometry.

HPLC retention time: 19.18 min. (The conditions were the same as those in example 1.)
TOF-MASS: [M+H]+471

EXAMPLE 15

(R)-N-tert-butyl-3-[(2S,3S)-2-hydroxy-3-[3-pyridylcarbonyl]amino-4-phenylbutanoyl]-1,3-thiazolidine-4-carboxamide To a suspension of (2S,3S)-H-AHPBA-Thz-NH-tBu (365 mg) and nicotinic acid (123 mg) in DMF (3 ml), EDC.HCl (192 mg) and HOBt.H$_2$O (153 mg) were added, which was stirred for 14 hours at room temperature, followed by concentration under reduced pressure to give residue containing product. The same purification as those in example 14 was carried out. The above-mentioned product (312 mg) was obtained. Said compound was identified as the desired compound by HPLC analysis and time of flight mass spectrometry.

HPLC retention time: 15.36 min. (The conditions were the same as those in example 1.)
TOF-MASS: [M+H]+471

EXAMPLE 16

(R)-N-tert-butyl-3-[(2S,3S)-2-hydroxy-3-[4-pyridylcarbonyl]amino-4-phenylbutanoyl]-1,3-thiazolidine-4-carboxamide To a suspension of (2S,3S)-H-AHPBA-Thz-NH-tBu (365 mg) and isonicotinic acid (123 mg) in DMF (3 ml), EDC.HCl (192 mg) and HOBt.H$_2$O (153 mg) were added, which was stirred for 14 hours at room temperature, followed by concentration under reduced pressure to give residue containing product. The same purification as those in example 14 was carried out.

The above-mentioned product (305 mg) was obtained. Said compound was identified as the desired compound by HPLC analysis and time of flight mass spectrometry.

HPLC retention time: 16.70 min. (The conditions were the same as those in example 1.)
TOF-MASS: [M+H]+471

EXAMPLE 17

(R)-N-tert-butyl-3-[(2S,3S)-2-hydroxy-3-[2-thienylcarbonyl]amino-4-phenylbutanoyl]-1,3-thiazolidine-4-carboxamide To a suspension of (2S,3S)-H-AHPBA-Thz-NH-tBu (365 mg) and 2-thiophene carboxylic acid (128 mg) in DMF (3 ml), EDC.HCl (192 mg) and HOBt.H$_2$O (153 mg) were added, which was stirred for 14 hours at room temperature, followed by concentration under reduced pressure to give residue containing product. The same purification as those in example 1 was carried out. The above-mentioned product (361 mg) was obtained. Said compound was identified as the desired compound by HPLC analysis and time of flight mass spectrometry.

HPLC retention time: 19.14 min. (The conditions were the same as those in example 1.)
TOF-MASS: [M+H]+476

EXAMPLE 18

(R)-N-tert-butyl-3-[(2S,3S)-2-hydroxy-3-[3-thienylcarbonyl]amino-4-phenylbutanoyl]-1,3-thiazolidine-4-carboxamide To a suspension of (2S,3S)-H-AHPBA-Thz-NH-tBu (365 mg) and 3-thiophene carboxylic acid (128 mg) in DMF (3 ml), EDC.HCl (192 mg) and HOBt.H$_2$O (153 mg) were added, which was stirred for 14 hours at room temperature, followed by concentration under reduced pressure to give residue containing product. The same purification as those in example 1 was carried out. The above-mentioned product (390 mg) was obtained. Said compound was identified as the desired compound by HPLC analysis and time of flight mass spectrometry.

HPLC retention time: 18.90 min.(The conditions were the same as those in example 1.)
TOF-MASS: [M+H]+476

EXAMPLE 19

(R)-N-tert-butyl-3-[(2S,3S)-2-hydroxy-3-[2-furylcarbonyl]amino-4-phenylbutanoyl]-1,3-thiazolidine-4-carboxamide To a suspension of (2S,3S)-H-AHPBA-Thz-NH-tBu (365 mg) and 1.4 2-furan carboxylic acid (112 mg) in DMF (3 ml), EDC.HCl (192 mg) and HOBt.H$_2$O (153 mg) were added, which was stirred for 14 hours at room temperature, followed by concentration under reduced pressure to give residue containing product. The same purification as those in example 1 was carried out. The above-mentioned product (372 mg) was obtained. Said compound was identified as the desired compound by HPLC analysis and time of flight mass spectrometry.

HPLC retention time: 18.16 min. (The conditions were the same as those in example 1.)
TOF-MASS: [M+H]+460

EXAMPLE 20

(R)-N-tert-butyl-3-[(2S,3S)-2-hydroxy-3-[3-furylcarbonyl]amino-4 -phenylbutanoyl]-1,3-thiazolidine-4-carboxamide To a suspension of (2S,3S)-H-AHPBA-Thz-NH-tBu (365 mg) and 3-furan carboxylic acid (112 mg) in DMF (3 ml), EDC.HCl (192 mg) and HOBt.H$_2$O (153 mg) were added, which was stirred for 14 hours at room temperature, followed by concentration under reduced pressure to give residue containing product. The same purification as those in example 1 was carried out. The above-mentioned product (331 mg) was obtained. Said compound was identified as the desired compound by HPLC analysis and time of flight mass spectrometry.

HPLC retention time: 18.36 min. (The conditions were the same as those in example 1.)
TOF-MASS: [M+H]+460

EXAMPLE 21

(R)-N-tert-butyl-3-[(2S,3S)-2-hydroxy-3-[3-hydroxy-2-methylbenzoyl]amino-4-phenylbutanoyl]-1,3-thiazolidine-4-carboxamide To a suspension of (2S,3S)-H-AHPBA-Thz-NH-tBu (365 mg) and 3-hydroxy-2-methylbenzoic acid (152 mg) in DMF (3 ml), EDC.HCl (192 mg) and HOBt.H$_2$O (153 mg) were added, which was stirred for 14 hours at room temperature, followed by concentration under reduced pressure to give residue containing product. The same purification as those in example 1 was carried out. The above-mentioned product (380 mg) was obtained. Said compound was identified as the desired compound by HPLC analysis, time of flight mass spectrometry and $^1$H-NMR.

HPLC retention time: 17.67 min. (The conditions were the same as those in example 1.)

TOF-MASS: [M+H]+500

FAB-MASS: [M+H]+500

$^1$H-NMR(DMSO-d$_6$) δ ppm: 1.26 (s;9H), 1.82 (s;3H), 2.74 (m;2H), 3.02 (m;1H), 3.32 (m;1H), 4.35 (bs;1H), 4.58 (bs;1H), 4.78 (m;2H), 5.09 (d;1H), 5.21 (d;1H), 6.56 (d;1H), 6.77 (d;1H), 6.94 (t;1H), 7.15 (t;1H), 7.23 (t;2H), 7.38 (d;2H), 7.64 (s;1H), 8.22 (d;1H), 9.38 (s;1H)

EXAMPLE 22

(R)-N-tert-butyl-3-[(2S,3S)-2-hydroxy-3-[3-hydroxy-2-methylbenzoyl]amino-4-phenylbutanoyl]-5,5-dimethyl-1,3-thiazolidine-4-carboxamide To a suspension of (2S,3S)-H-AHPBA-Dmt-NH-tBu (197 mg) and 3-hydroxy-2-methylbenzoic acid (76.1 mg) in DMF (1.5 ml), EDC.HCl (96 mg) and HOBt.H$_2$O (76.5 mg) were added, which was stirred for 14 hours at room temperature, followed by concentration under reduced pressure to give residue containing product. The same purification as those in example 1 was carried out. The above-mentioned product (174 mg) was obtained. Said compound was identified as the desired compound by HPLC analysis, time of flight mass spectrometry and $^1$H-NMR.

HPLC retention time: 18.97 min. (The conditions were the same as those in example 1.)

TOF-MASS: [M+H]+528

FAB-MASS: [M+H]+528

$^1$H-NMR (DMSO-d$_6$) δ ppm: 1.27 (s;9H), 1.40 (s;3H), 1.49 (s;3H), 1.80 (s;3H), 2.75 (m;2H), 3.2–3.4 (m;1H), 4.35 (bs;1H), 4.52 (bs and s;2H), 4.98 (d;1H), 5.18 (d;1H), 5.27 (d;1H), 6.55 (d;1H), 6.76 (d;1H), 6.94 (t;1H), 7.13 (t;1H), 7.23 (t;2H), 7.36 (d;2H), 7.63 (s;1H), 8.22 (d;1H), 9.3 (s;1H)

EXAMPLE 23

(R)-N-tert-butyl-3-[(2S,3S)-2-hydroxy-3-[3-carbamoylbenzoyl]amino-4-phenylbutanoyl]-1,3-thiazolidine-4-carboxamide To a solution of (R)-N-tert-butyl-3-[(2S,3S)-2-hydroxy-3-[2-carboxybenzoyl]amino-4-phenylbutanoyl]-1,3-thiazolidine-4-carboxamide (145 mg) dissolved in DMF (2 ml), EDC.HCl (54.3 mg) and HOBt.H$_2$O (43.3 mg) were added, which was stirred for 1 hour at room temperature. After the reaction, to the reaction mixture, 25% ammonium aqueous solution (19.2 μl) was added and kept stirred for 14 hours at room temperature, followed by concentration under reduced pressure to give residue containing product. The same purification as those in example 1 was carried out. The above-mentioned compound (122 mg) was obtained. Said compound was identified as the desired compound by HPLC analysis and time of flight mass spectrometry.

HPLC retention time: 16.38 min. (The conditions were the same as those in example 1.)

TOF-MASS: [M+H]+513

EXAMPLE 24

N-tert-butyl-1-[(2S,3S)-2-hydroxy-3-N-[3-hydroxy-2-methylbenzoyl]amino-4-phenylbutanoyl]-L-prolinamide To a suspension of (2S,3S)-H-AHPBA-Pro-NH-tBu (347 mg) and 3-hydroxy-2-methyl benzoic acid (152 mg) in DMF (5 ml), EDC.HCl (192 mg) and HOBt.H$_2$O (135 mg) were added, which was stirred for 14, hours at room temperature, followed by concentration under reduced pressure to give residue containing product. The same purification as those in example 1 was carried out. The above-mentioned product (276 mg) was obtained. Said compound was identified as the desired compound by HPLC analysis and time of flight mass spectrometry.

HPLC retention time: 16.80 min. (The conditions were the same as those in example 1.)

TOF-MASS: [M+H]+482

EXAMPLE 25

(R)-N-tert-butyl-3-[(2S,3S)-2-hydroxy-3-[3-amino-2-methylbenzoyl]amino-4-phenylbutanoyl]-1,3-thiazolidine-4-carboxamide To a suspension of (2S,3S)-H-AHPBA-Thz-NH-tBu (365 mg) and 3-amino-2-methylbenzoic acid (151 mg) in DMF (4 ml), EDC.HCl (211 mg) and HOBt.H$_2$O (153 mg) were added, which was stirred for 14 hours at room temperature, followed by concentration under reduced pressure to give residue containing product. The same purification as those in example 1 was carried out. The above-mentioned product (153 mg) was obtained. Said compound was identified as the desired compound by HPLC analysis and time of flight mass spectrometry.

HPLC retention time: 14.57 min. (The conditions were the same as those in example 1.)

TOF-MASS: [M+H]+499

EXAMPLE 26

(R)-N-tert-butyl-3-[(2S,3S)-2-hydroxy-3-(2,3-dimethylbenzoyl]amino-4-phenylbutanoyl]-4-carboxamide To a suspension of (2S,3S)-H-AHPBA-Thz-NH-tBu (365 mg) and 2,3-dimethyl benzoic acid (150 mg) in DMF (4 ml), EDC.HCl (201 mg) and HOBt.H$_2$O(153 mg) were added, which was stirred for 14 hours at room temperature, followed by concentration under reduced pressure to give residue containing product. The same purification as those in example 1 was carried out. The above-mentioned compound (280 mg) was obtained. Said compound was identified as the desired compound by HPLC analysis and time of flight mass spectrometry.

HPLC retention time: 19.77 min. (The conditions were the same as those in example 1.)

TOF-MASS: [M+H]+498

EXAMPLE 27

(R)-N-tert-butyl-3-[(2S,3S)-2-hydroxy-3-[2-amino-3-hydroxybennzoyl]amino-4-phenylbutanoyl]-1,3-thiazolidine-4-carboxamide To a suspension of (2S,3S)-H-AHPBA-Thz-NH-tBu (365 mg) and 2-amino-3-hydroxybenzoic acid (168 mg) in DMF (4 ml), EDC.HCl (211 mg) and HOBt.H$_2$O (168 mg) were added, which was stirred for 14 hours at room temperature, followed by concentration under reduced pressure to give residue containing product. The same purification as those in example 1 was carried out. The above-mentioned compound (130 mg) was obtained. Said compound was identified as the desired compound by HPLC analysis and time of flight mass spectrometry.

HPLC retention time: 15.55 min. (The conditions were the same as those in example 1.)
TOF-MASS: [M+H]+501

EXAMPLE 28

(R)-N-tert-butyl-3-[(2S,3S)-2-hydroxy-3-(2-methyl-3-hydroxybenzoyl)amino-4-phenylbutanoyl]-1,3-thiazolidine-1,1-dioxide-4-carboxamide Process 1
(R)-N-tert-butyl-3-[(2S,3S)-3-(tert-butoxycarbonyl)amino-2-hydroxy-4-phenylbutanoyl]-1,3-thiazolidine-1,1-dioxide-4-carboxamide To a mixture of Boc-AHPBA-Thz-NH-tBu (1.40 g; 3.0 mmol), MeOH (24 ml): $H_2O$ (12 ml), OXONE (2.17 g; 3.6 mmol) was added which was stirred for 14 hours at room temperature. The reaction mixture was extracted after adding dichioromethane and water. Separated organic layer was washed with 5% brine solution and dried over magnesium sulphate anhydride, followed by concentration thereof under reduced pressure. Obtained crystal by recrystallization of the residue from toluene/n-hexane was further purified by silica gel chromatography (ethyl acetate/n-hexane). Again, the obtained residue was further purified by recrstallization from toluene/n-hexane. The above mentioned compound(0.25 g, yield 17%) was recovered.

Process 2
(R) -N-tert-butyl-3-[(2S,3S)-2-hydroxy-3-(2-methyl-3-hydroxybenzoyl]amino-4-phenylbutanoyl]-1,3-thiazolidine-1,1-dioxide-4-carboxamide.

To Boc-AHPBA-Thz($O_2$)-NH-tBu (200 mg) obtained in process 1, 4N-HCl/dioxane solution (2 ml) was added and the mixture was stirred for 3 hours at room temperature, followed by concentration to give residue, which was dissolved in DMF (6 ml) and neutralized with triethylamine (0.06 ml). Thereto, 3-hydroxy-2-methylbenzoic acid (64 mg), EDC.HCl (84 mg) and HOBt.$H_2O$ (64 mg) were added, which was stirred for 14 hours at room temperature, followed by concentration under reduced pressure to give residue containing product. The same purification as those in example 1 was carried out. The above-mentioned compound (60 mg) was obtained. Said compound was identified as the desired compound by HPLC analysis and time of flight mass spectrometry.

HPLC retention time: 16.52 min. (The conditions were the same as those in example 1.)
TOF-MASS: [M+H]+532

EXAMPLE 29

(R)-N-tert-butyl-3-[(2S,3S)-2-hydroxy-3-(3,5-dihydroxybenzoyl)amino-4-phenylbutanoyl]-1,3-thiazolidine-4-carboxamide To a suspension of (2S,3S)-H-AHPBA-Thz-NH-tBu (365 mg) and 3,5-dihydroxybenzoic acid (170 mg) in DMF (5 ml), EDC.HCl (211 mg) and HOBt.$H_2O$ (168 mg) were added, which was stirred for 14 hours at room temperature, followed by concentration under reduced pressure to give residue containing product. The same purification as those in example 1 was carried out. The above-mentioned compound (70 mg) was obtained. Said compound was identified as the desired compound by HPLC analysis and time of flight mass spectrometry.

HPLC retention time: 15.68 min. (The conditions were the same as those in example 1.)
TOF-MASS: [M+H]+502

EXAMPLE 30

(4S,5R)-N-tert-butyl-3-[(2S,3S)-2-hydroxy-3-(2-methyl-3-hydroxybenzoyl)amino-4-phenylbutanoyl]-5-methyl-1,3-oxazolidine-4-carboxamide Process 1
(4S,5R)-3-tert-butoxycarbonyl-4-N-tert-butylcarbamoyl-5-methyl-1, 3-oxazolidine A mixture of (4S,5R)-3-tert-butoxycarbonyl-5-methyl-1, 3-oxazolidine-4-caboxylic acid, Boc-Oxz(Me)-OH (4.13 g), HOSu (2.06 g) and EDC.HCl (3.76 g) dissolved in 100 ml of dichloromethane was stirred for 2 hours at room temperature, followed by adding 3.75 ml tert-butylamine and stirring it for another 3 hours. The reaction mixture was washed with 3% $Na_2CO_3$ aqueous solution, 1N-HCl and 5% NaCl aqueous solution consecutively and dried over magnesium sulphate anhydride. After evaporation of the solvent, recrystallization of the obtained residue from n-hexane to yield 3.94 g of above-mentioned compound (yield 77%). Said compound was identified to be the desired compound by $^1$H-NMR spectroscopy.

$^1$H-NMR (DMSO-$d_6$): δ ppm:1.26 (s,9H), 1.39 (s,9H), 3.7–3.8 (br,1H), 4.1–4.2 (br,2H), 4.72 (br,1H)), 4.82 (br, 1H)), 7.53 (br,1H)).

Process 2
(2S,3S)-3-tert-butoxycarbonylamino-2-hydroxy-4-phenylbutanoic acid benzylester A mixture of Boc-AHPBA-OH.DCHA (4.76 g) and 1.19 ml of benzyl bromide dissolved in 20 ml of DMF was stirred overnight (about 14 hours) at room temperature. The reaction mixture was filtrated and the filtrate was concentrated. The obtained residue was dissolved in ethyl acetate and washed with 5% citric acid aqueous solution, 3% disodium carbonate aqueous solution and 5% brine solution consecutively and dried over magnesium sulphate anhydride. Recrystallization of the residue from n-hexane to yield 3.11 g of the desired compound (yield 81%).

Process 3
(2S,3S)-3-(2-methyl-3-hydroxybenzoyl)amino-2-hydroxy-4-phenylbutanoic acid benzyl ester A solution of Boc-AHPBA-OBzl (1.15 g) obtained in process 2 and 4N-HCl/dioxane (20 ml) in 20 ml of dichloromethane was stirred for 3 hours at room temperature.

The reaction mixture was concentrated and obtained residue was dissolved in 30 ml of DMF and neutralized with 0.42 ml of $Et_3N$, following by adding 3-hydroxy-2-methyl benzoic acid (0.46 g), HOBt.$H_2O$ (0.46 g) and EDC.HCl (0.63 g) and stirring it overnight (about 14 hours) at room temperature. Then, the reaction mixture was stirred after addition of dichloromethane and 5% sodium bicarbonate aqueous solution thereto. The organic layer (dichloromethane layer) was separated and washed with 5% sodium bicarbonate aqueous solution, 1N-HCl and 5% brine solution consecutively. During this operation, crystalline precipitate from organic layer was recovered by filtration. The filtrate was dried over magnesium sulphate anhydride and concentrated to give the residue, which was also recovered. Recrystallization of precipitated crystalline combined with the residue yielded 0.71 g of the desired compound (yield 56%).

Process 4
(2S,3S)-3-(2-methyl-3-hydroxybenzoyl)amino-2-hydroxy-4-phenylbutanoic acid Into a solution of (3-hydroxy-2-methylbenzoyl)-AHPBA-OBzl (0.64 g) obtained in process 3 in 20 ml of methanol, hydrogen gass was introduced in the presence of 10% Pd/C (30 mg) overnight (for about 14 hours). The reaction mixture was filtrated and the filtrate was concentrated. Recrystallization of the residue from acetone/n-hexane to yield 0.56 g of the above-mentioned compound (yield 100%). Said compound was identified to be the desired compound by $^1$H-NMR spectroscopy and time of flight mass spectrometry.,

TOF-MASS:[M+H]+330

$^1$H-NMR(CDCl$_3$) δ ppm: 1.98 (s;3H), 2.91 (d;2H,J=7.5 Hz), 4.34 (d;1H,J=3.6 Hz), 4.74 (m;1H), 6.60 (d;1H,J=7.5 Hz), 6.91 (dd;1H,J=7.5 Hz,7.5 Hz), 7.1–7.3(m;5H), 7.62 (s;1H), 8.8–9.0 (br;1H)

Process 5

(4S,5R)-N-tert-butyl-3-[(2S,3S)-2-hydroxy-3-(2-methyl-3-hydroxybenzoyl)amino-4-phenylbutanoyl]-5-methyl-1,3-oxazolidine-4-carboxamide A mixture of Boc-Oxz (Me)-NHtBu (286 mg) and 4N-HCl/dioxane (2.5 ml) was stirred for 3 hours at room temperature. After evaporation of the solvent, obtained residue was dissolved in 4 ml of DMF and neutralized with Et$_3$N (0.14 ml), followed by adding (3-hydroxy-2 methylbenzoyl)-AHPBA-OH (362 mg), HOBt.H$_2$O (164 mg), EDC.HCl (211 mg) and stirring it for 14 hours at room temperature. The reaction mixture was concentrated under reduced pressure to give residue containing product. Purification was carried out in the same manner as those in example 1 to yield the above-mentioned compound (210 mg). Said compound was identified to be the desired compound by, HPLC analysis, $^1$H-NMR spectroscopy and time of flight mass spectrometry.

HPLC retention time: 15.55 min. (The conditions are the same as those in example 1.)

TOF-MASS: [M+H]+501

$^1$H-NMR (DMSO-d$_6$)δ ppm: 1.27 (s;9H), 1.32 (d;3H, J=5.1 Hz), 1.60 (s;3H), 4.00 (m;3H), 4.28 (br;3H), 5.06 (d;1H, J=5.4 Hz), 5.43 (d;1H, J=3.6 Hz), 5.55 (d;1H, J=6.4 Hz), 6.57 (d; 1H, J=8.9 Hz), 6.78 (d;1H, J=8.9 Hz), 6.94 (dd;1H, J=37.9 Hz, 7.9 Hz), 7.16 (d;1H, J=7.5 Hz), 7.24 (t;2H,J=7.5 Hz, 7.5 Hz), 7.33 (d;2H, J=7.5 Hz), 7.74 (s;1H), 8.15 (d;1H, J=7.9 Hz), 9.34 (s;1H)

EXAMPLE 31

(R)-N-tert-butyl-3-[(2S,3S)-2-hydroxy-3-(2-ethyl-3-hydroxybenzoyl)amino-4-phenylbutanoyl]-1,3-thiazolidine-4-carboxamide To a suspension of (2S,3S)-H-AHPBA-Thz-NHtBu (365 mg) and 2-ethyl-3-hydroxybenzoic acid (183 mg), EDC.HCl (211 mg) and HOBt.H$_2$O (168 mg) were added, which was stirred for 14 hours at room temperature.

The reaction mixture was concentrated under reduced pressure to give residue containing product. Purification was carried out in the same manner as those in example 1 to yield the above-mentioned compound (319 mg). Said compound was identified to be the desired compound by HPLC analysis, $^1$H-NMR and time of flight mass spectrometry.

HPLC retention time: 17.28 min. (The conditions are the same as those in example 1.)

TOF-MASS: [M+H]+514

$^1$H-NMR(DMSO-d$_6$) δ ppm: 0.85 (t;3H, J=7.5 Hz, 7.5 Hz), 1.25 (s;9H), 2.35 (m;2H), 2.74 (m;2H), 3.00 (m;1H), 3.20–3.40 (m;1H), 4.35 (br;1H), 4.55 (br;1H), 4.77 (m;2H), 5.05 (d;1H, J=9.3 Hz), 5.25 (d;1H, J=7.1 Hz), 6.5 (d;1H, J=7.1 Hz), 6.78 (d;1H, J=8.6 Hz), 6.94 (dd;1H, J=7.9 Hz, 9 Hz), 7.18 (d;1H, J=6.6 Hz), 7.22 (t;2H, J=7.1 Hz, 7.1 Hz), 7.38 (d;2H, J=7.5 Hz), 7.63 (s;1H), 8.21(d;1H, J=7.9 Hz), 9.31 (s;1H)

EXAMPLE 32

(R)-N-tert-butyl-3-[(2S,3S)-2-hydroxy-3-(3-hydroxy-2-propylbenzoyl)amino-4-phenylbutanoyl]-1,3-thiazolidine-4-carboxamide To a suspension of (2S,3S)-H-AHPBA-Thz-NHtBu (365 mg) and 3-hydroxy-2-propylbenzoic acid (168 mg) in 4 ml of DMF,EDC.HCl (211 mg) and HOBt.H$_2$O (168 mg) were added, which was stirred for 14 hours at room temperature. The reaction mixture was concentrated under reduced pressure to give residue containing product. Purification was carried out in the same manner as those in example 1 to yield the desired compound (130 mg). Said compound was identified to be the above-mentioned compound by HPLC analysis and time of flight mass spectrometry.

HPLC retention time: 18.04 min. (The conditions are the same as those in example 1.)

TOF-MASS: [M+H]+528

EXAMPLE 33

(R)-N-tert-butyl-3-[(2S,3S)-2-hydroxy-3-(3,5-diamino-2-methylbenzoyl)amino-4-phenylbutanoyl]-1,3-thiazolidine-4-carboxamide Process 1

(R)-N-tert-butyl-3-[(2S,3S)-2-hydroxy-3-(2-methyl-3,5-dinitrobenzoyl)amino-4-phenylbutanoyl]-1,3-thiazolidine-4-carboxamide To a suspension of (2S,3S)-H-AHPBA-Thz-NHtBu (1.10 g) and 2-methyl-3,5-dinitrobenzoic acid (3,5-dinitro-o-toluic acid/0.75 g) in 15 ml of DMF, EDC.HCl (0.63 g) and HOBt.H$_2$O (0.45 g) were added, which was stirred for 14 hours at room temperature. The reaction mixture was concentrated under reduced pressure to give residue containing product. Purification was carried out in the same manner as those in example 1 to yield the above-mentioned compound (1.08 g). Said compound was identified to be the desired compound by HPLC and time of flight mass spectrometry.

HPLC retention time: 19.42 min. (The conditions are the same as those in example 1.)

TOF-MASS: [M+H]+574

Process 2

(R)-N-tert-butyl-3-[(2S,3S)-2-hydroxy-3-(3,5-diamino-2-methylbenzoyl)amino-4-phenylbutanoyl]-1,3-thiazolidine-4-carboxamide (R)-N-tert-butyl-3-[(2S,3S)-2-hydroxy-3-(2-methyl-3,5-dinitrobenzoyl)amino-4-phenylbutanoyl]-1,3-thiazolidine-4-carboxamide (287 mg) was dissolved in ethanol (10 ml) and iron powder (279 mg) and 10% acetic acid aqueous solution (15 ml) was dropped thereto, followed by stirring it for 1 hour at 50° C., adding 5 ml of 1N-HCl and 40 ml of 5% bicarbonate aqueous solution and adjusting to pH 7.5. The reaction mixture was extracted with dichloromethane (40 ml). The extract was dried over magnesium sulphate anhydride and was concentrated under reduced pressure to give residue containing product. The residue was purified by silica gel chromatography to give 30 mg of crude product, which was, further, purified by prepartive HPLC to yield the above-mentioned compound (15 mg). Said compound was identified to be the desired compound by HPLC and time of flight mass spectrometry.

HPLC retention time: 13.45 min. (The conditions are the same as those in example 1.)

TOF-MASS: [M+H]+514

EXAMPLE 34

(R)-N-(2-methylbenzyl)-3-[(2S,3S)-3-(3-hydroxy-2-methylbenzoyl) amino-2-hydroxy-4-phenylbutanoyl]-1,3-thiazolidine-4-carboxamide Process 1
(R)-N-(2-methylbenzyl)-1,3-thiazolidine-4-carboxamide (H-Thz-NH-Bz 1(2-Me))

To a solution of Boc-Thz-OH (6.99 g) and HOBt.H$_2$O (4.05 g) in 100 ml of CH$_2$Cl$_2$, EDC.HCl (6.30 g) was added, which was stirred for 3 hours at room temperature, followed by adding 2-methylbenzyl amine (4.46 ml) thereto and stirring it overnight (for about 14 hours).

The reaction mixture was washed with 3% sodium carbonate aqueous solution, 1N-HCl and 5% brine solution consecutively and dried over magnesium sulphate anhydride. After evaporation of the solvent, the residue was, again, dissolved in 100 ml of dichloromethane, followed by the addition of methane sulfonic acid (5.86 ml) thereto and stirring it for 1 hour at room temperature.

Then, 150 ml of water was added thereto and stirred and water layers were separated. The separated water layer was extracted with 100 ml of dichloromethane at pH 8 adjusted with sodium carbonate. The separated dichloromethane layer was washed with 5% brine solution and dried over magnesium sulphate anhydride. After evaporation of the solvent, recrystallization of the obtained residue from ethyl acetate/n-hexane to yield 6.04 g of the above-mentioned compound (yield 85%).

$^1$H-NMR(DMSO-d$_6$) δ ppm: 2.56 (s,3H), 2.85–3.05 (m,3H), 3.2–3.4 (m,1H), 3.86 (m,1H), 4.0–4.2 (m,2H), 4.2–4.3 (br,2H), 7.0–7.2 (br,4H), 8.34 (br,1H)

Process 2
(R)-N-(2-methylbenzyl)-3-[(2S,3S)-3-amino-2-hydroxy-4-phenylbutanoyl]-1,3-thiazolidine-4-carboxamide((2S,3S)-H-AHPBA-Thz-NH-Bzl(2-Me))

To a solution of H-Thz-NH-Bzl(2-Me) (5.83 g), Boc-AHPBA-OH (7.29 g) and HOBt.H$_2$O (3.34 g) in 100 ml of CH$_2$Cl$_2$, EDC.HCl (5.19 g) were added, which was stirred for 14 hours at room temperature. The reaction mixture was washed with 3% sodium carbonate aqueous solution, 1N-HCl and 5% brine solution consecutively and dried over magnesium sulphate anhydride. After evaporation of the solvent, the residue was, again, dissolved in 150 ml of dichloromethane, followed by the addition of methane sulfonic acid (4.82 ml) thereto and stirring it for 1 hour at room temperature.

Then, 150 ml of water and 14.8 ml of 5N-NaOH aqueous solution were added thereto and stirred and two layers were separated. The dichloromethane layer was washed with 5% saline solution and dried over magnesium sulphate anhydride. After evaporation of the solvent, the residue was dissolved in 150 ml hot ethyl acetate and insoluble substance was removed by filtration, followed by evaporation of solvent to obtain crude product powder (7.00 g) was obtained. 2.00 g of the powder was purified silica gel chromatography (dichloromethane/MeOH) to give the rough-purified product. Recrystallization of the obtained rough-purified product from ethyl acetate/n-hexane to yield 1.48 g of the above-mentioned compound (yield 52%).

$^1$H-NMR(CDCl$_3$) δ ppm: 0.2–1.4 (br,2H), 2.20 (s,3H), 2.2–2.4 (m,1H), 2.4–2.6 (m,1H), 3.14 (d,2H, J=16.8 Hz), 3.21 (t,1H, J=5.4 Hz), 3.48 (d;1H, J=9.6 Hz), 3.94 (d;1H, J=9.6 Hz), 4.1–4.3 (m,1H), 4.3–4.5 (m,1H), 4.55 (d,1H, J=7.5 Hz), 6.8–7.1 (m,6H), 7.1–7.4 (m,3H), 7.9–8.1 (br,1H)

Process 3
(R)-N-(2-methylbenzyl)-3-[(2S,3S)-3-(3-hydroxy-2-methylbenzoyl)amino-2-hydroxy-4-phenylbutanoyl]-1,3-thiazolidine-4-carboxamide To a suspension of (2S,3S)-H-AHPBA-Thz-NH-Bzl(2-Me) (414 mg) and 3-hydroxy-2-methyl benzoic acid (167 mg) in 4 ml of DMF, EDC (211 mg) and HOBt (149 mg) were added, which was stirred for 14 hours at room temperature. The reaction mixture was concentrated under reduced pressure to give residue containing product. Purification was carried out in the same manner as discribed in example 1 to yield the above-mentioned compound (500 mg). Said compound was identified to be the desired compound by $^1$H-NMR and time of flight mass spectrometry as described below.

HPLC retention time: 19.34 min. (The conditions are the same as those in example 1.)

TOF-MASS: [M+H]+548

$^1$H-NMR(DMSO-d$_6$) δ ppm: 1.83 (s;3H), 2.23 (s;3H), 2.78 (m;2H), 3.10 (m;1H), 3.20–3.40 (m;1H), 4.18 (d; 1H, J=6.0 Hz), 4.30 (d;1H, J=7.1 Hz), 4.38 (m;2H), 4.78 (d;1H, J=8.7 Hz), 4.87 (t;1H, J=6.4 Hz, 6.4 Hz), 5.03 (d;1H, J=10.0 Hz), 5.45 (d;1H, J=6.4 Hz), 6.55 (d;1H, J=7.2 Hz), 6.77 (d;1H, J=8.1 Hz), 6.93 (dd;1H, J=6.4 Hz, 6.4 Hz), 7.12 (bs;4H), 7.23 (bs;3H), 7.32(d;2H, J=6.0 Hz), 8.15(d;1H, J=7.9 Hz), 8.35 (br;1H), 9.37 (s;1H)

EXAMPLE 35

(R)-N-(2-methylbenzyl)-3-[(2S,3S)-3-(2-ethyl-3-hydroxybenzoyl)amino-2-hydroxy-4-phenylbutanoyl]-1,3-thiazolidine-4-carboxamide Using (2S,3S)-H-AHPBA-Thz-NH-Bzl(2-Me) (414 mg) and 2-ethyl-3-hydroxybenzoic acid (167 mg), condensation and purification were carried out in the same manner as discribed in example 1 to yield the above-mentioned compound (500 mg). Said compound was identified to be the desired compound by HPLC and time of flight mass spectrometry as described below.

HPLC retention time: 19.61 min. (The conditions are the same as those in example 1.)

TOF-MASS: [M+H]+562

EXAMPLE 36

(R)-N-tert-butyl-3-[((2S,3S)-3-(2-ethyl-3-hydroxybenzoyl)amino-2-hydroxy-4-phenylbutanoyl]-5,5-dimethyl-1,3-thiazolidine-4-carboxamide Using (2S,3S)-H-AHPBA-Dmt-NHtBu (414 mg) and 2-ethyl-3-hydroxybenzoic acid (167 mg), condensation and purification were carried out in the same manner as discribed in example 1 to yield the above-mentioned compound (500 mg). Said compound was identified to be the desired compound by HPLC analysis and time of flight mass spectrometry as described below.

HPLC retention time: 19.61 min. (The conditions are the same as those in example 1.)

TOF-MASS: [M+H]+542

EXAMPLE 37

(R)-N-(2-methylbenzyl )-3-[(2S,3S)-3-(3-hydroxy-2-methylbenzoyl)amino-2-hydroxy-4-phenylbutanoyl]-5,5-dimethyl-1,3-thiazolidine-4-carboxamide Using (2S,3S)-H-AHPBA-Dmt-NH-Bzl(2-Me) (414 mg) and 3-hydroxy-2-methylbenzoic acid (167 mg), condensation and purification were carried out in the same manner as

EXAMPLE 38

(R)-N-(2-methylbenzyl)-3-[(2S,3S)-3-(2-ethyl-3-hydroxybenzoyl)amino-2-hydroxy-4-phenylbutanoyl]-5,5-dimethyl-1,3-thiazolidine-4-carboxamide Using (2S,3S)-H-AHPBA-Dmt-NH-Bzl(2-Me) (414 mg) and 2-ethyl-3-hydroxybenzoic acid (167 mg), condensation and purification were carried out in the same manner as discribed in example 1 to yield the above-mentioned compound (500 mg). Said compound was identified to be the desired compound by HPLC analysis and time of flight mass spectrometry as described below.

HPLC retention time: 19.61 min. (The conditions are the same as those in example 1.)

TOF-MASS: [M+H]+590

EXAMPLE 39

(R)-N-n-butyl-3-[(2S,3S)-3-(3-hydroxy-2-methylbenzoyl)amino-2-hydroxy-4-phenylbutanoyl)-1,3-thiazolidine-4-carboxamide.

Using (2S,3S)-H-AHPBA-Thz-NHnBu (183 mg) and 3-hydroxy-2-methylbenzoic acid (76 mg), condensation and purification were carried out in the same manner as discribed in example 1 to yield the above-mentioned compound (160 mg). Said compound was identified to be the desired compound by HPLC analysis and time of flight mass spectrometry as described below.

HPLC retention time: 17.24 min. (The conditions are the same as those in example 1.)

TOF-MASS: [M+H]+500

EXAMPLE 40

(2S,4S)-N-tert-butyl-3-[(2S,3S)-3-(2-methyl-3-hydroxybenzoyl)amino-2-hydroxy-4-phenylbutanoyl] -4-chloropyrrolidine-2-caroxamide Using Boc-Pro[4(S)-Cl]-NHtBu (152 mg) and (2S,3S)-(3-hydroxy-2-methylbenzoyl-AHPBA-OH (173 mg), condensation and purification were carried out in the same manner as those in example 30 to yield the above-mentioned compound (240 mg). Said compound was identified to be the desired compound by HPLC analysis and time of flight mass spectrometry as described below.

HPLC retention time: 17.95 min. (The conditions are the same as those in example 1.)

TOF-MASS: (M+H]+517

EXAMPLE 41

(2S,4S)-N-(2-methylbenzyl)-3-[(2S,3S)-3-(3-hydroxy-2-methylbenzoyl)amino-2-hydroxy-4-phenylbutanoyl]-4-chloropyrrolidine-2-carboxamide Using Boc-Pro[4(S)-Cl]-NHBzl(2-Me) (171 mg) and (3-hydroxy-2-methylbenzoyl-AHPBA-OH (168 mg), condensation and purification were carried out in the same manner as those in example 30 to yield the above-mentioned compound (230 mg). Said compound was identified to be the desired compound by HPLC analysis and time of flight mass spectrometry as described below.

HPLC retention time: 20.44 min. (The conditions are the same as those in example 1.)

TOF-MASS: [M+H]+564

EXAMPLE 42

(R)-N-(2-chlorobenzyl)-3-[(2S,3S)-3-(3-hydroxy-2-methylbenzoyl)amino-2-hydroxy-4-phenylbutanoyl]-1,3-thiazolidine-4-carboxamide Using Boc-AHPBA-Thz-NHBzl(2-Cl) (276 mg) and 2-methyl-3-hydroxybenzoic acid (83 mg), condensation and purification were carried out in the same manner as those in example 30 to yield the above-mentioned compound (160 mg). Said compound was identified to be the desired compound by HPLC analysis and time of flight mass spectrometry as described below.

HPLC retention time: 20.06 min. (The conditions are the same as those in example 1.)

TOF-MASS: [M+H]+569

EXAMPLE 43

(2S,4S)-N-tert-butyl-3-[(2S,3S)-3-(2-ethyl-3-hydroxybenzoyl)amino-2-hydroxy-4-phenylbutanoyl]-4-chloropyrolidine-2 -carboxamide Using Boc-AHPBA-Pro[4(S)Cl]-NHtBu (429 mg) and 2-ethyl-3-hydroxybenzoic acid (155 mg), condensation and purification were carried out in the same manner as in example 32 to yield the above-mentioned compound (328 mg). Said compound was identified to be the desired compound by HPLC and time of flight mass spectrometry as described below.

HPLC retention time: 20.33 min. (the conditions are the same as in example 1)

TOF-MASS: [M+H]$^+$531

EXAMPLE 44

(R)-N-(2,6-dimethylbenzyl)-3-[(2S,3S)-3-(3-hydroxy-2-methylbenzoyl)amino-2-hydroxy-4-phenylbutanoyl]-1,3-thiazolidine-4-carboxamide Using (3-hydroxy-2-methylbenzoyl)-AHPBA-OH prepared from 173 mg of 3-hydroxy-2-methylbenzoic acid in the same manners as in example 30 and H-Thz-NH-Bzl(2, 6-Me)(125 mg), condensation and purification were carried out to yield the above-mentioned compound (234 mg). Said compound was identified to be the desired compound by HPLC and time of flight mass spectrometry as described below.

HPLC retention time: 20.69 min. (the conditions are the same as in example 1)

TOF-MASS: [M+H]$^+$562

EXAMPLE 45

(R)-N-(2-chlorobenzyl)-3-[(2S,3S)-3 -(3-hydroxy-2-methylbenzoyl)amino-2-hydroxy-4-phenylbutanoyl]-5,5-dimethylthiazolidine-4-carboxamide Using (2S,3S)-H-AHPBA-Dmt-NH-Bzl(2-Cl) (138 mg) and 3-hydroxy-2-methylbenzoic acid (50 mg), condensation

--- those in example 1 to yield the above-mentioned compound (500 mg). Said compound was identified to be the desired compound by HPLC analysis and time of flight mass spectrometry as described below.

HPLC retention time: 19.89 min. (The conditions are the same as those in example 1.)

TOF-MASS: [M+H]+576 and purification were carried out in the same manner as in example 1 to yield the above-mentioned compound (100 mg). Said compound was identified to be the desired compound by HPLC and time of flight mass spectrometry as described below.

HPLC retention time: 20.91 min. (the conditions are the same as in example 1)

TOF-MASS: [M+H]$^+$597

In order to confirm that the dipeptide compound of the present invention has characteristics suitable for medicinal use, for example, an excellent HIV protease inhibitory activity and lowercytotoxicity etc., the following tests were carried out.

TEST EXAMPLE 1

HIV protease inhibitory activity

According to a method which was already reported in publications (Yoshiaki Kiso, Yuuki-gosei-kagaku-kyokai-shi, vol. 52, 403–412 (1994), Japanese laid-open patent, No. 170722(1993), etc.), the compounds of example 1–42 were evaluated to verify high HIV protease inhibitory activity of the dipeptide compound of the present invention. As a positive control, KNI-272 which was already reported to exhibit high HIV protease inhibitory activity (Yoshiaki Kiso, Yuuki-gosei-kagaku-kyokai-shi, vol 52, 403–412 (1994)) was also evaluated for comparison.

Test method

Recombinant HIV protease (Biochemistry, 250 (9), 264 (1990)) and synthetic hepta-peptide (H-Ser-Gln-Asn-Tyr-Pro-Ile-Val-OH/ trifluoroacetic acid salt) were used for assay of protease activity. Peptide fragment H-Pro-Ile-Val-OH formed by cleavage between -Tyr . . . Pro of said substrate after a reaction in the presence of various concentration of tested compound at 37° C. for 60 min. was determined by reversed phase HPLC and the inhibitory rate was calculated (referred to Japanese laid-open unexamined patent, No. 170722/1993).

Some examples of the evaluation results of HIV protease inhibitory activity of the dipeptide compound of the present invention according to the above-mentioned method were summarized in Table 1 which also includes the evaluation results of KNI-272[(R)-3-[(2S,3S)-3-(N-(isoquinoline-5-yloxy)acetyl-methylthio-L-alanyl)amino-2-hydroxy-4-phenylbutanoyl]1,3-thiazolidine-4-N'-t-butylcarboxamide as another positive control which is a hydroxymethylcarboxamide type of tripeptide similar to the dipeptide compound of the present invention and has (2S,3S)-3-amino-2-hydroxy-4-phenylbutanoyl residue. As the evaluation results showed, any of the peptide compounds of the present invention exhibited high HIV protease inhibitory activity. The concentration of tested compound represents the final concentration thereof of the reaction mixture.

TABLE 1

| Tested compound | HIV protease inhibitory activity (%) Concentration | |
|---|---|---|
| | [5 µM] | [50 nM] |
| Compound of example 1 | 52.0 | |
| Compound of example 2 | 74.9 | |
| Compound of example 6 | 76.0 | |
| Compound of example 7 | 62.2 | |

TABLE 1-continued

| Tested compound | HIV protease inhibitory activity (%) Concentration | |
|---|---|---|
| | [5 µM] | [50 nM] |
| Compound of example 13 | 70.4 | |
| Compound of example 21 | 96.7 | 36.1 |
| Compound of example 22 | 99.0 | 87.6 |
| Compound of example 24 | 94.2 | 17.6 |
| Compound of example 25 | 81.3 | |
| Compound of example 26 | 77.9 | |
| Compound of example 27 | 93.0 | 13.4 |
| Compound of example 28 | 96.1 | 23.8 |
| Compound of example 29 | 75.6 | |
| Compound of example 30 | 96.9 | 21.5 |
| Compound of example 31 | 97.5 | 45.6 |
| Compound of example 32 | 92.0 | 17.2 |
| Compound of example 33 | 85.2 | |
| Compound of example 34 | 96.7 | 69.8 |
| Compound of example 35 | 98.1 | 48.8 |
| Compound of example 36 | >99.0 | 83.5 |
| Compound of example 37 | >99.0 | 95.8 |
| Compound of example 38 | >99.0 | 97.3 |
| Compound of example 39 | 92.0 | 13.4 |
| Compound of example 40 | 96.2 | 68.2 |
| Compound of example 41 | 97.7 | 76.8 |
| Compound of example 42 | 97.4 | 51.2 |
| Compound of example 43 | 96.7 | 67.6 |
| Compound of example 44 | 97.9 | 75.2 |
| Compound of example 45 | >99.0 | 94.5 |
| (Compound as a positive control) KNI 272 | >99.0 | 96.7 |

TEST EXAMPLE 2

Anti-HIV activity and cytotoxicity

The anti-HIV activity of the dipeptide compound of the present invention was evaluated as described below. That is, the inhibitory action of the compound on formation of HIV virus particles which infects T lymphocyte was evaluated by potency to prevent death of T lymphocyte accompanied by said virus infection.

Test method for anti-HIV activity and cytotoxicity

According to a test method which was already reported in publications (H. Nakashima et al., Antimicrob. Agents Chemother.36, 1249–1255 (1992), etc.,), anti-HIV activity was evaluated, by using MT-4 cell line and HTLV-IIIB virus, MT-4 cells ($2.5 \times 10^4$ well, MOI:001) infected with said HTLV-IIIB virus just before the addition were into 96-well microtiter plate wherein each well contained various concentration of tested compound. At the same time, in order to investigate cytotoxicity of tested compounds to MT-4 cell line, non-infected MT-4 cell line was cultured in the presence of various kinds of tested compound. After 5 day culture at 37° C. in a $CO_2$ incubator, the number of vial cells was counted by MTT method.

Anti-HIV activity was expressed by the concentration at which it protect 50% of cytotoxicity by HIV infection ($EC_{50}$, 50% effective concentration): cytotoxicity was expressed by the concentration exhibiting 50% cytotoxicity by tested compound ($CC_{50}$, 50% cytotoxic concentration). Virus whose infectious value was $3.8 \times 10^4$ TCID 50/ml was used.

Evaluation examples of $EC_{50}$ of anti-HIV activity and of $CC_{50}$ of cytotoxicity were disclosed in table 2 which also includes the evaluation results of KNI-272 as positive control. As the results showed, it was clear that the peptide compounds of the present invention had anti-HIV activity. In addition, it was also clear that they showed lower cytotoxicity. That is, the concentration to reveal cytotoxicity is much higher than the concentration to prevent effectively HIV virus infection.

TABLE 2

| Tested compound | Anti-HIV activity $EC_{50}$ (μg/ml) | Cytotoxicity $CC_{50}$ (μg/ml) |
|---|---|---|
| Compound of example 21 | 0.70 | 184 |
| Compound of example 22 | 0.15 | 156 |
| Compound of example 24 | 1.97 | 231 |
| Compound of example 28 | 1.80 | 146 |
| Compound of example 30 | 1.40 | 191 |
| Compound of example 31 | 1.46 | 168 |
| Compound of example 34 | 5.35 | 24.5 |
| Compound of example 35 | 4.15 | 90.9 |
| Compound of example 36 | 0.54 | 103 |
| Compound of example 38 | 0.18 | 19.5 |
| (Compound of positive control) KNI-272 | 0.21 | 115 |

TEST EXAMPLE 3

Pharmacokinetics

Metabolic characteristics of the dipeptide compounds of the present invention was evaluated using rats. Tested compounds dissolved in vehicle was administered intraduodenally or intravenously. After administration, blood was taken and the concentration of residual tested compound in plasma was analyzed. The dosage of the tested compound was described in table 3. Pharmacokinetical such as AUC (Area under the curve), MRT (Mean residence time), $t_{1/2}(\lambda)$ (half life) and parameter F (bioavailability on intraduodenal administration) were also disclosed in table 3, wherein results of tripeptide derivative KNI-272 were also disclosed as control.

TABLE 3

| Tested compound | Dosage (mg/kg) | AUC (μg/ml/min) | MRT (min) | $t_{1/2}$ (λ) (min) | F (%) |
|---|---|---|---|---|---|
| Compound of example 21 | | | | | |
| i. v. | 10.0 | 111 | 31.7 | 35.98 | — |
| i. d. | 20.0 | 101 | | | 45.41 |
| Compound of example 22 | | | | | |
| i. v. | 10.0 | 111 | 22.9 | 23.89 | — |
| i. d. | 20.0 | 106 | | | 47.53 |
| Compound of example 31 | | | | | |
| i. v. | 10.0 | 276 | 96.0 | 73.81 | — |
| i. d. | 10.0 | 99 | | | 36.24 |
| Compound of example 34 | | | | | |
| i. v. | 10.0 | 124 | 31.9 | 40.51 | — |
| i. d. | 10.0 | 40 | | | 32.26 |
| Compound of example 36 | | | | | |
| i. v. | 10.0 | 174 | 88.9 | 83.90 | — |
| i. d. | 10.0 | 64 | | | 37.01 |
| Compound of example 37 | | | | | |
| i. v. | 10.0 | 131 | 74.7 | 92.63 | — |
| i. d. (control) | 10.0 | 55 | | | 41.55 |

TABLE 3-continued

| Tested compound | Dosage (mg/kg) | AUC (μg/ml/min) | MRT (min) | $t_{1/2}$ (λ) (min) | F (%) |
|---|---|---|---|---|---|
| KNI-272 | | | | | |
| i. v. | 10.0 | 224 | 23.2 | 25.57 | — |
| i. d. | 10.0 | 98 | | | 43.20 | i. v. means intravenous administration
i. d. means intraduodenal administration

As the results showed, it became clear that plasma high level of the dipeptide of the present invention could be maintained for longer duration than KNI-272 as control because of its stability in vivo.

EXAMPLE 43

Pharmaceutical preparation

The dipeptide compound of the present invention can be orally administered according to the prescription described below, such as, capsules. For example, pharmaceutical preparation comprising the compound of example 21 as an effective ingredient can be prepared as capsules by packing fine powder lactose, magnesium stearate into a gelatin capsule whose composition was described in table 4. The amount of said peptide-like compound in a capsule can be selected depending on administration route or dosing duration.

TABLE 4

| Composition in a capsule | |
|---|---|
| Compound of example 21 | 20.0% (wt./wt.) |
| Lactose | 79.5% (wt./wt.) |
| Magnesium stearate | 0.5% (wt./wt.) |

We claim:
1. A dipeptide compound or pharmaceutically acceptable salt thereof comprising the formula (I):

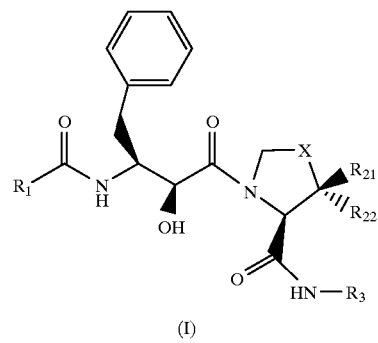

Formula I (I)

wherein $R_1$ represents a 5-membered or 6-membered monocyclic hydrocarbon group or heterocyclic group wherein 3 or fewer substituents other than hydrogen are present on said cyclic group;

X represents a methylene group (—$CH_2$—), a chloromethylene group (—CH(Cl)—), an oxygen atom, a sulfur atom or a sulfonyl group (—$SO_2$—);

$R_{21}$ and $R_{22}$ each represents a hydrogen atom or a linear or branched aliphatic hydrocarbon group having 1–6 carbon atoms; and $R_3$ represents a linear or branched aliphatic hydrocarbon group having 1–6 carbon atoms or a monovalent group comprising an aromatic monocyclic hydrocarbon group having 12 or fewer carbon atoms in total, wherein a halogen atom can be substituted on the aromatic ring of the aromatic monocyclic hydrocarbon group.

2. A dipeptide compound or pharmaceutically acceptable salt thereof comprising the formula (II):

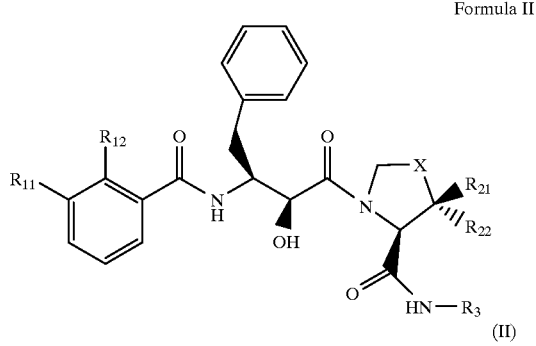

Formula II (II)

wherein X represents a methylene group (—CH$_2$—), a chloromethylene group (—CH(Cl)—), an oxygen atom, a sulfur atom or a sulfonyl group (—SO$_2$);

$R_{21}$ and $R_{22}$ each represents a hydrogen atom or a linear or branched aliphatic hydrocarbon group having 1–6 carbons;

$R_3$ represents a linear or branched aliphatic hydrocarbon group having 1–6 carbon atoms or a monovalent group comprising an aromatic monocyclic hydrocarbon group having 12 or fewer carbon atoms, wherein a halogen atom can be substituted on the aromatic ring of said aromatic monocyclic hydrocarbon group;

$R_{11}$ represents a hydrogen atom, an amino group or a hydroxyl group; and $R_{12}$ represents a hydrogen atom or a linear or branched aliphatic hydrocarbon group having 1–4 carbon atoms.

3. A dipeptide compound or pharmaceutically acceptable salt comprising the formula (III):

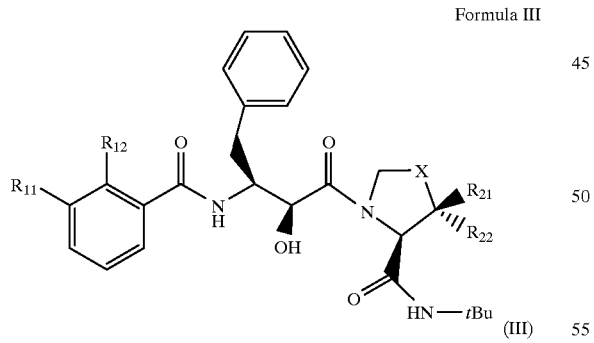

Formula III (III)

wherein X represents a methylene group (—CH$_2$—), a chloromethylene group (—CH(Cl)—), an oxygen atom, a sulfur atom or a sulfonyl group (—SO$_2$);

$R_{21}$ and $R_{22}$ each represents a hydrogen atom or a linear or branched aliphatic hydrocarbon group 1–6 carbon atoms;

$R_{11}$ represents a hydrogen atom, an amino group or a hydroxyl group; and $R_{12}$ represents a hydrogen atom or a linear or branched aliphatic hydrocarbon group having 1–4 carbon atoms.

4. A dipeptide compound or pharmaceutically acceptable salt thereof comprising the formula (IV):

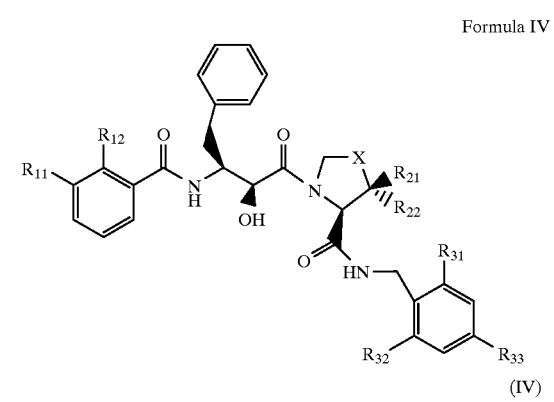

Formula IV (IV)

wherein X represents a methylene group (—CH$_2$—), a chloromethylene group (—CH(Cl)—), an oxygen atom, a sulfur atom or a sulfonyl group (—SO$_2$);

$R_{21}$ and $R_{22}$ each represents a hydrogen atom or a linear or branched aliphatic hydrocarbon group 1–6 carbon atoms;

$R_{11}$ represents a hydrogen atom, an amino group or a hydroxyl group;

$R_{12}$ represents a hydrogen atom or a linear or branched aliphatic hydrocarbon group having 1–4 carbon atoms; and $R_{31}$, $R_{32}$ and $R_{33}$ each represents a hydrogen atom, a halogen atom, or a linear or branched aliphatic hydrocarbon group having 14 carbons.

5. A dipeptide compound or pharmaceutically acceptable salt thereof comprising the formula (V):

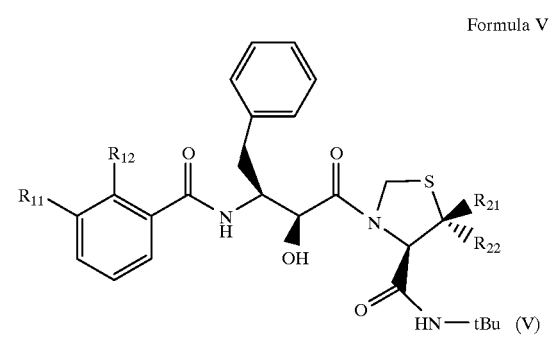

Formula V (V)

wherein $R_{11}$ represents an amino group or a hydroxyl group; $R_{12}$ represents a methyl group or an ethyl group; and $R_{21}$ and $R_{22}$ each represents a hydrogen atom or a methyl group.

6. A dipeptide compound or pharmaceutically acceptable salt thereof comprising the formula (VI):

Formula VI

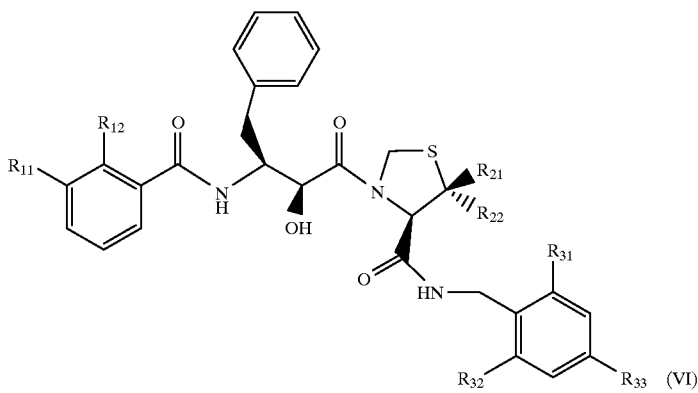

wherein $R_{11}$ represents an amino group or a hydroxyl group; $R_{12}$ represents a methyl group or an ethyl group; $R_{21}$ and $R_{22}$ each represents a hydrogen atom or a methyl group; and $R_{31}$, $R_{32}$ and $R_{33}$ each represents a hydrogen atom, a halogen atom or a methyl group.

7. The dipeptide compound or pharmaceutically acceptable salt thereof of claim 1 wherein X is a sulfur atom.

8. The dipeptide compound or pharmaceutically acceptable salt thereof of claim 2 wherein X is a sulfur atom.

9. The dipeptide compound or pharmaceutically acceptable salt thereof of claim 3 wherein X is a sulfur atom.

10. The dipeptide compound or pharmaceutically acceptable salt thereof of claim 4 wherein X is a sulfur atom.

11. The dipeptide compound or pharmaceutically acceptable salt thereof of claim 4 wherein X is a sulfur atom;

$R_{21}$ and $R_{22}$ each represents a methyl group;

$R_{31}$ represents a methyl group;

$R_{32}$ and $R_{33}$ each represents a hydrogen atom;

$R_{11}$ represent a hydroxyl group; and $R_{12}$ represents a methyl group.

12. The dipeptide compound or pharmaceutically acceptable salt thereof of claim 1 wherein X represents a methylene group (—$CH_2$—), an oxygen atom, or a sulfonyl group (—$SO_2$—).

13. The dipeptide compound or pharmaceutically acceptable salt thereof of claim 2 wherein X represents a methylene group (—$CH_2$—), an oxygen atom, or a sulfonyl group (—$SO_2$—).

14. The dipeptide compound or pharmaceutically acceptable salt thereof of claim 3 wherein X represents a methylene group (—$CH_2$—), an oxygen atom, or a sulfonyl group (—$SO_2$—).

15. The dipeptide compound or pharmaceutically acceptable salt thereof of claim 4 wherein X represents a methylene group (—$CH_2$—), an oxygen atom, or a sulfonyl group (—$SO_2$—).

16. An anti-HIV agent comprising an effective amount of the dipeptide compound or pharmaceutically acceptable salt thereof as in one of claims 1–15 to inhibit HIV protease activity.

* * * * *

UNITED STATES PATENT AND TRADEMARK OFFICE
CERTIFICATE OF CORRECTION

PATENT NO.   : 5,932,550
DATED        : August 3, 1999
INVENTOR(S)  : Kato et al.

Page 1 of 1

It is certified that error appears in the above-identified patent and that said Letters Patent is hereby corrected as shown below:

Claim 2,
Line 6, delete "(—$SO_2$)" and replace it with -- )—$SO_2$—) --; and
Line 9, delete "carbons" and replace it with -- carbon atoms --.

Claim 3,
Line 2, insert -- thereof -- between "salt" and "comprising";
Line 6, delete "(—$SO_2$)" and replace it with -- (—$SO_2$—) --; and
Line 8, insert -- having -- between "group" and "1-6".

Claim 4,
Line 6, delete "(—$SO_2$)" and replace it with -- (—$SO_2$—) --;
Line 8, insert -- having -- between "group" and "1-6"; and
Line 17, delete "14" and replace it with -- 1-4 --.

Signed and Sealed this

Thirty-first Day of July, 2001

*Attest:*

Nicholas P. Godici

*Attesting Officer*

NICHOLAS P. GODICI
*Acting Director of the United States Patent and Trademark Office*